(12) United States Patent
Wham

(10) Patent No.: US 10,058,374 B2
(45) Date of Patent: Aug. 28, 2018

(54) SYSTEMS AND METHODS FOR ESTIMATING TISSUE PARAMETERS USING SURGICAL DEVICES

(71) Applicant: COVIDIEN LP, Mansfield, MA (US)

(72) Inventor: Robert H. Wham, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 844 days.

(21) Appl. No.: 14/297,890

(22) Filed: Jun. 6, 2014

(65) Prior Publication Data
US 2015/0088125 A1 Mar. 26, 2015

Related U.S. Application Data

(60) Provisional application No. 61/882,675, filed on Sep. 26, 2013, provisional application No. 61/882,678, (Continued)

(51) Int. Cl.
*A61B 18/12* (2006.01)
*A61B 18/00* (2006.01)
(Continued)

(52) U.S. Cl.
CPC ...... *A61B 18/1233* (2013.01); *A61B 18/1206* (2013.01); *A61B 18/1445* (2013.01); (Continued)

(58) Field of Classification Search
CPC ............ A61B 18/1206; A61B 18/1233; A61B 18/1445; A61B 18/1815; (Continued)

(56) References Cited

U.S. PATENT DOCUMENTS 5,507,743 A * 4/1996 Edwards ................ A61N 5/045
600/373
5,891,134 A * 4/1999 Goble .................... A61B 18/08
606/191

(Continued)

FOREIGN PATENT DOCUMENTS

DE 179607 C 3/1905
DE 390937 C 3/1924
(Continued)

OTHER PUBLICATIONS

European Search Report issued in corresponding EP Application No. 14186605.3 dated Feb. 3, 2015.
(Continued)

*Primary Examiner* — Daniel Fowler

(57) ABSTRACT

Systems and methods for estimating tissue parameters, including mass of tissue to be treated and a thermal resistance scale factor between the tissue and an electrode of an energy delivery device, are disclosed. The method includes sensing tissue temperatures, estimating a mass of the tissue and a thermal resistance scale factor between the tissue and an electrode, and controlling an electrosurgical generator based on the estimated mass and the estimated thermal resistance scale factor. The method may be performed iteratively and non-iteratively. The iterative method may employ a gradient descent algorithm that iteratively adds a derivative step to the estimates of the mass and thermal resistance scale factor until a condition is met. The non-iterative method includes selecting maximum and minimum temperature differences and estimating the mass and the thermal resistance scale factor based on a predetermined reduction point from the maximum temperature difference to the minimum temperature difference.

17 Claims, 13 Drawing Sheets

Related U.S. Application Data filed on Sep. 26, 2013, provisional application No. 61/882,680, filed on Sep. 26, 2013.

(51) Int. Cl.
  A61B 18/14 (2006.01)
  A61B 18/18 (2006.01)

(52) U.S. Cl.
  CPC ... *A61B 18/1815* (2013.01); *A61B 2018/0063* (2013.01); *A61B 2018/00577* (2013.01); *A61B 2018/00648* (2013.01); *A61B 2018/00702* (2013.01); *A61B 2018/00791* (2013.01); *A61B 2018/00827* (2013.01); *A61B 2018/00875* (2013.01); *A61B 2018/00892* (2013.01)

(58) Field of Classification Search
  CPC .. A61B 2018/00577; A61B 2018/0063; A61B 2018/00648; A61B 2018/00702; A61B 2018/00791; A61B 2018/00827; A61B 2018/00875; A61B 2018/00892
  See application file for complete search history.

(56) References Cited

U.S. PATENT DOCUMENTS

| | | | |
|---|---|---|---|
| D574,323 | S | 8/2008 | Waaler |
| 2005/0137588 | A1* | 6/2005 | McGaffigan ......... A61B 18/085 606/29 |
| 2009/0157071 | A1* | 6/2009 | Wham ............... A61B 18/1206 606/33 |
| 2010/0137854 | A1 | 6/2010 | Hosier |
| 2012/0136354 | A1* | 5/2012 | Rupp ................ A61B 18/1206 606/51 |
| 2013/0103023 | A1 | 4/2013 | Monson et al. |
| 2013/0215216 | A1 | 8/2013 | Friedrichs et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2409661 A1 | 1/2012 |
| EP | 2457532 A1 | 5/2012 |
| EP | 2620115 A1 | 7/2013 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | H06500476 A | 1/1994 |
| JP | 2002-065690 A | 3/2002 |
| JP | 2005-185657 A | 7/2005 |
| JP | 2007229454 A | 9/2007 |
| JP | 2012115669 A | 6/2012 |
| SU | 166452 | 11/1964 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |

OTHER PUBLICATIONS

Extended European Search Report for EP 14 18 4738 dated Apr. 10, 2015.
U.S. Appl. No. 14/297,812 dated Jun. 6, 2014, inventor: Wham.
U.S. Appl. No. 14/297,890 dated Jun. 6, 2014, inventor: Wham.
U.S. Appl. No. 14/320,762 dated Jul. 1, 2014, inventor: Gilbert.
U.S. Appl. No. 14/320,804 dated Jul. 1, 2014, inventor: Gilbert.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.

(56) References Cited

OTHER PUBLICATIONS

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/168,296 dated Jan. 30, 2014, inventor: Mattmiller.
U.S. Appl.No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/255,051 dated Apr. 17, 2014 inventor: Coulson.
U.S. Appl. No. 14/262,219 dated Apr. 25, 2014, inventor: Gilbert.
U.S. Appl. No. 14/267,066 dated May 1, 2014, inventor: Friedrichs.
U.S. Appl. No. 14/268,187 dated May 2, 2014, inventor: Kerr.
U.S. Appl. No. 14/283,604 dated May 21, 2014, inventor: Behnke.
U.S. Appl. No. 14/297,771 dated Jun. 6, 2014, inventor: Wham.
Japanese Office Action dated Jun. 7, 2018 in corresponding Japanese Patent Application No. 2014-190955 with English translation.
Australian Examination Report dated Jun. 19, 2018 in Australian Patent Application No. 2014218375.

* cited by examiner

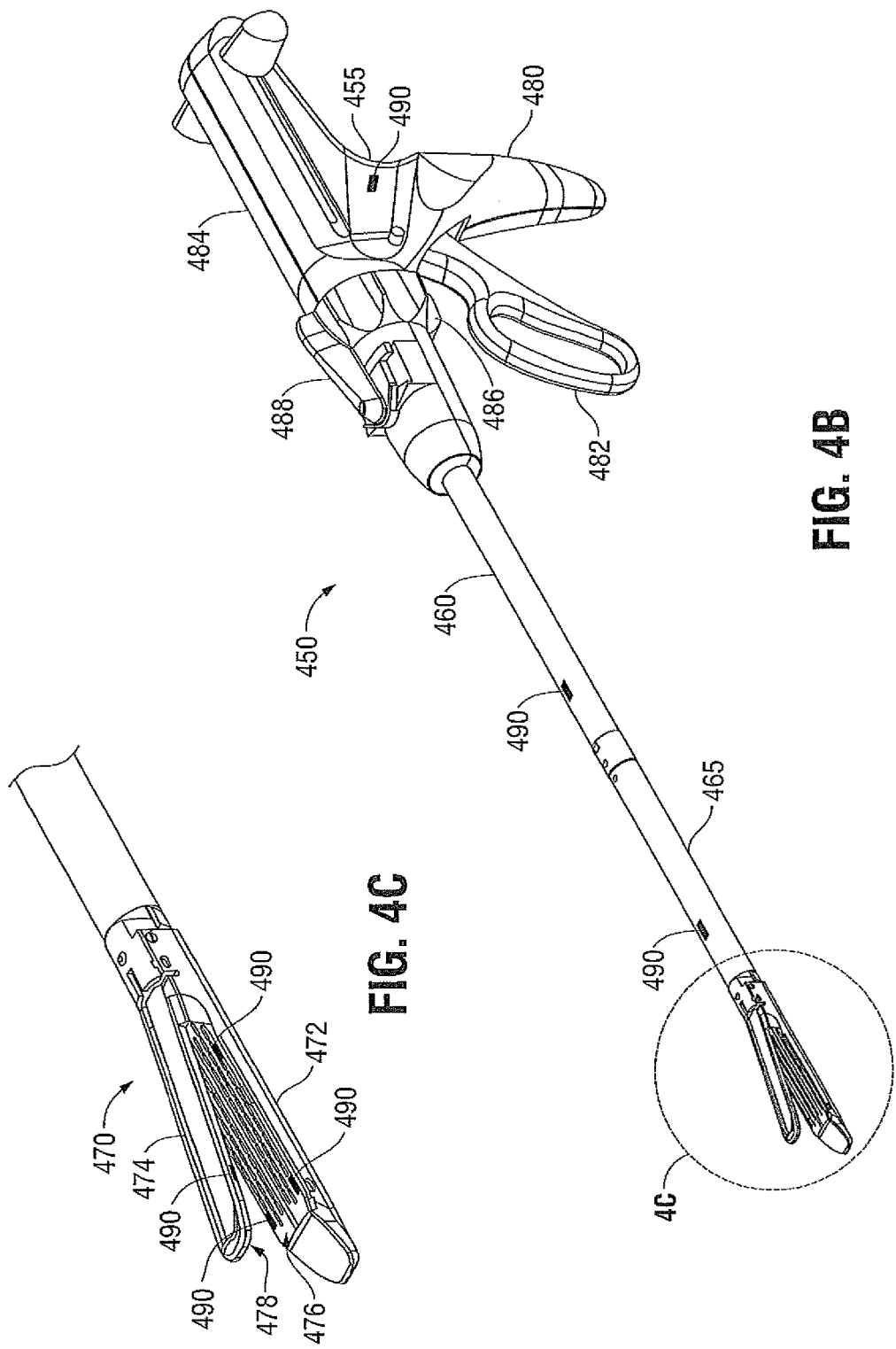

SYSTEMS AND METHODS FOR ESTIMATING TISSUE PARAMETERS USING SURGICAL DEVICES

CROSS-REFERENCE TO RELATED APPLICATIONS

This application claims the benefit of and priority to U.S. Provisional Application No. 61/882,675, filed on Sep. 26, 2013, U.S. Provisional Application No. 61/882,678, filed on Sep. 26, 2013, and U.S. Provisional Application No. 61/882,680, filed on Sep. 26, 2013. This application is related to U.S. patent application Ser. No. 14/297,771, filed on Jun. 6, 2014, and U.S. patent application Ser. No. 14/297,812, filed on Jun. 6, 2014. The entire contents of the above applications are incorporated herein by reference.

BACKGROUND

1. Technical Field

The present disclosure relates to estimating tissue parameters. More particularly, the present disclosure relates to systems and methods for estimating tissue parameters, such as tissue mass, via surgical devices and controlling these surgical devices based on the estimated tissue parameters.

2. Background of Related Art

There are many types of surgical devices that may be used to treat tissue in a variety of surgical procedures. One type of surgical device is a linear clamping, cutting, and stapling device. This device may be employed in a surgical procedure to resect a cancerous or anomalous tissue from a gastrointestinal tract. Conventional linear clamping, cutting and stapling instruments include a pistol grip-styled structure having an elongated shaft. The distal portion of the elongated shaft includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion of the elongated shaft also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

Another type of surgical device is an electrosurgical device which is employed in an electrosurgical system for performing electrosurgery. Electrosurgery involves the application of high-frequency electric current to cut or modify biological tissue. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The alternating current typically has a frequency above 100 kilohertz (kHz) to avoid muscle and/or nerve stimulation.

During electrosurgery, AC generated by the electrosurgical generator is conducted through tissue disposed between the active and return electrodes. The tissue's impedance converts the electrical energy (also referred to as electrosurgical energy) associated with the AC into heat, which causes the tissue temperature to rise. The electrosurgical generator controls the heating of the tissue by controlling the electric power (i.e., electrical energy per unit time) provided to the tissue. Although many other variables affect the total heating of the tissue, increased current density usually leads to increased heating. The electrosurgical energy is typically used for cutting, dissecting, ablating, coagulating, and/or sealing tissue.

The two basic types of electrosurgery employed are monopolar and bipolar electrosurgery. Both types of electrosurgery use an active electrode and a return electrode. In bipolar electrosurgery, the surgical instrument includes an active electrode and a return electrode on the same instrument or in very close proximity to one another, usually causing current to flow through a small amount of tissue. In monopolar electrosurgery, the return electrode is located elsewhere on the patient's body and is typically not a part of the energy delivery device itself. In monopolar electrosurgery, the return electrode is part of a device usually referred to as a return pad.

An electrosurgical generator includes a controller that controls the power applied to a load, i.e., the tissue, over some period of time. The power applied to the load is controlled based upon the power determined at the output of the electrosurgical generator and a power level set by the user or a power level needed to achieve a desired effect on the tissue. The power may also be controlled based on other parameters of the tissue being treated such as tissue temperature.

SUMMARY

The systems and methods of the present disclosure estimate the mass of tissue and a thermal resistance scale factor or a thermal coefficient between the tissue and a surgical instrument, such as sealing jaw members of an electrosurgical instrument. In the case of electrosurgery, the level of power supplied to the tissue may be controlled based on the estimated mass of the tissue. Estimation can be performed by commonly available microprocessors, field programmable gate arrays (FPGAs), digital signal processors (DSPs), application specific integrated circuits (ASICs), or programmable DSPs.

In one aspect, the present disclosure features a method of determining a tissue parameter. The method includes generating a test signal using a generator, providing a test signal to tissue using an energy delivery device, sensing voltage and current waveforms of the test signal, calculating an impedance of the tissue and a change in the tissue impedance based on the sensed voltage and current waveforms, estimating a temperature of the tissue and a change in the tissue temperature based on the calculated impedance and the change in the tissue impedance, and a heat transfer model, and estimating the mass of the tissue based on the estimated tissue temperature.

The method further includes estimating mass of the tissue based on the estimated tissue temperature, determining a time at which the tissue temperature remains substantially constant, estimating tissue temperature at the determined time, estimating a heat transfer coefficient of the tissue based on the estimated tissue temperature, and determining a tissue parameter based on the estimated mass of the tissue, the estimated heat transfer coefficient, and known parameters of the energy delivery device that delivers the test signal to the tissue.

The generator may be a microwave generator and the energy deliver device may be a microwave ablation applicator, or the generator may be an electrosurgical generator and the energy delivery applicator may be an electrosurgical instrument.

The known parameters include the surface area of an electrode of an electrosurgical instrument that contacts the tissue, the mass of the electrode, and the heat transfer coefficient of the electrode.

In yet another aspect, the present disclosure features a method of determining a tissue parameter. The method includes generating a test signal using a generator, providing the test signal to the tissue via an energy delivery device, estimating a first impedance of the tissue, estimating a first change in temperature of the tissue based on a heat transfer model at a first time based on the first tissue impedance, estimating a second impedance of the tissue, estimating a second change in temperature of the tissue based on a heat transfer model at a second time based on the second tissue impedance, estimating mass of the tissue based on the first change in tissue temperature, estimating a heat transfer coefficient of the tissue based on the first and second changes in tissue temperature, and determining a tissue parameter based on the estimated mass of the tissue and the estimated heat transfer coefficient The mass and the heat transfer coefficient are estimated based on a system of second-order differential equations of changes in tissue temperature.

The energy delivery device may be a vessel sealing device.

BRIEF DESCRIPTION OF THE DRAWINGS

Various embodiments of the present disclosure are described with reference to the accompanying drawings wherein:

FIG. 4B is a perspective view of a stapling instrument and FIG. 4C is an expanded view of the distal tip of the stapling instrument of FIG. 4B according to embodiments of the present disclosure;

DETAILED DESCRIPTION

Figure 1:
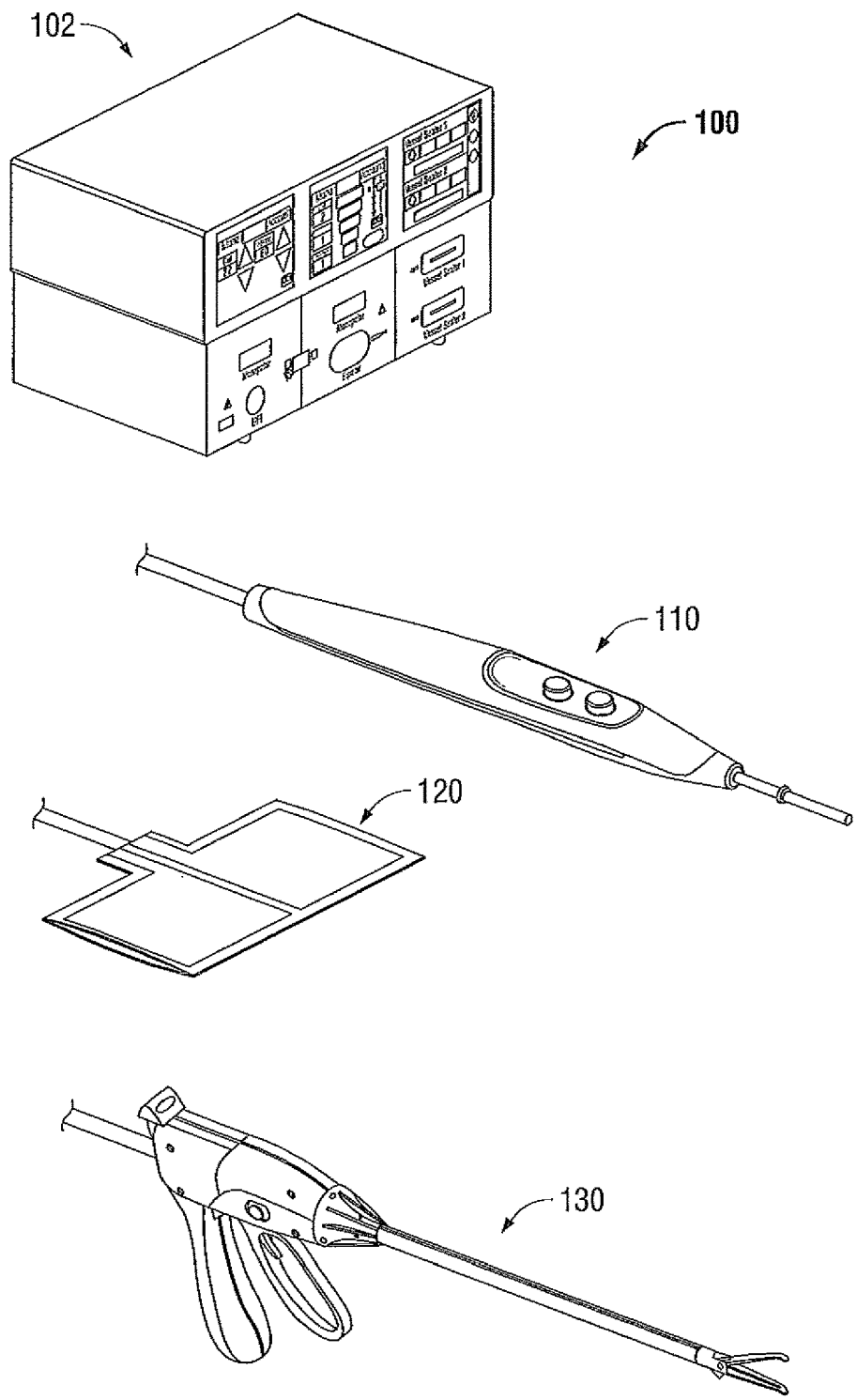
FIG. 1 is an illustration of an electrosurgical system in accordance with embodiments of the present disclosure.

For sealing algorithms, it is desirable to determine the mass of tissue grasped between the jaw members of an electrosurgical instrument, because the tissue mass is one of the main variations during sealing. In general, smaller masses need a small amount of energy to avoid over cooking, while larger masses need more energy to achieve a tissue temperature within a reasonable amount of time. Also, tissue temperature and pressure are significant factors which determine seal performance.

It is also desirable to determine tissue temperature during the seal procedure without expensive temperature sensors built into the sealing instruments. This can be accomplished by determining the thermal resistance scale factors or the heat transfer coefficients between the tissue and the seal plates, which is dependent on the surface area of the tissue. Once the thermal resistance scale factors or heat transfer coefficients are determined, then the tissue temperature can be modeled using a known input energy.

The systems and methods according to the present disclosure estimate the mass of tissue being treated based on the changes in tissue impedance and determine the thermal resistance scale factor (k) or the thermal coefficient of heat transfer between the tissue being treated and the energy delivery device, e.g., the seal plate, so that tissue temperature can be estimated over a cycle of an electrosurgical procedure, e.g., a sealing cycle. The mass of the tissue, the thermal resistance scale factor (k), and the thermal coefficient of heat transfer are estimated by modeling the temperatures of the tissue and the energy delivery device that is used to transmit electrosurgical energy to the tissue using a set or system of differential equations.

The set of differential equations incorporates physical characteristics of the tissue and the energy delivery device. The physical characteristics include the specific heat of the tissue, the heat conductivity between the tissue and electrodes or antennas of the energy delivery device, and the relationship between changes in tissue resistance and the energy supplied to the tissue. The estimated mass, the estimated thermal resistance scale factor, and/or the estimated thermal coefficient of heat transfer may be incorporated into algorithms for controlling energy delivery to the tissue.

The estimated mass and the estimated thermal coefficient of heat transfer or the thermal resistance scale factor may also be used to predict tissue temperature up to the point of loss of mass (either water or tissue). Once it is determined that there is a loss of mass, the mass and the thermal coefficient of heat transfer, or the thermal resistance scale factor may be further estimated to determine the loss in mass and to predict temperature above the boiling point of water or heat-related tissue mass loss (e.g., due to squeezing tissue between the jaw members of the electrosurgical forceps).

Estimates of the tissue mass may also be useful in surgical procedures that employ surgical staplers. The tissue mass may be used to determine the tissue thickness or size so that the surgical stapler and its staples can be properly configured to staple the tissue. Otherwise, if the tissue is too thin, a normal size staple may damage the tissue and, if the tissue is too thick, a normal size staple may not be effective for stapling the tissue.

Estimates of tissue mass may also be used in ablation procedures to adjust the microwave energy delivered to the tissue. Otherwise, too much energy delivered to a small mass would damage surrounding tissue and too little energy delivered to a large mass would not be sufficient for ablating tissue.

As described above, the systems and methods for estimating tissue mass and the thermal coefficient of heat transfer or the thermal resistance scale factor may be incorporated into any type of surgical device for treating tissue. For purposes of illustration and in no way limiting the scope of the appended claims, the systems and methods for estimating tissue mass and the thermal coefficient of heat transfer or the thermal resistance scale factor are described in the present disclosure in the context of electrosurgical systems.

FIG. 1 illustrates an electrosurgical system 100 in accordance with some embodiments of the present disclosure. The electrosurgical system 100 includes an electrosurgical generator 102 which generates electrosurgical energy to treat tissue of a patient. The electrosurgical generator 102 generates an appropriate level of electrosurgical energy based on the selected mode of operation (e.g., cutting, coagulating, ablating, or sealing) and/or the sensed voltage and current waveforms of the electrosurgical energy. The electrosurgical system 100 may also include a plurality of output connectors corresponding to a variety of energy delivery devices, e.g., electrosurgical instruments.

The electrosurgical system 100 further includes a number of energy delivery devices. For example, system 100 includes monopolar electrosurgical instrument 110 having an electrode for treating tissue of the patient (e.g., an electrosurgical cutting probe or ablation electrode, also known as an electrosurgical pencil) with a return pad 120. The monopolar electrosurgical instrument 110 can be connected to the electrosurgical generator 102 via one of the plurality of output connectors. The electrosurgical generator 102 may generate electrosurgical energy in the form of radio frequency (RF) energy. The electrosurgical energy is supplied to the monopolar electrosurgical instrument 110, which applies the electrosurgical energy to treat the tissue. The electrosurgical energy is returned to the electrosurgical generator 102 through the return pad 120. The return pad 120 provides a sufficient contact area with the patient's tissue so as to minimize the risk of tissue damage due to the electrosurgical energy applied to the tissue.

The electrosurgical system 100 also includes a bipolar electrosurgical instrument 130. The bipolar electrosurgical instrument 130 can be connected to the electrosurgical generator 102 via one of the plurality of output connectors. The electrosurgical energy is supplied to one of the two jaw members of the bipolar electrosurgical instrument 130, is applied to treat the tissue, and is returned to the electrosurgical generator 102 through the other of the two jaw members.

The electrosurgical generator 102 may be any suitable type of generator and may include a plurality of connectors to accommodate various types of electrosurgical instruments (e.g., monopolar electrosurgical instrument 110 and bipolar electrosurgical instrument 130). The electrosurgical generator 102 may also be configured to operate in a variety of modes, such as ablation, cutting, coagulation, and sealing. The electrosurgical generator 102 may include a switching mechanism (e.g., relays) to switch the supply of RF energy among the connectors to which various electrosurgical instruments may be connected. For example, when an electrosurgical instrument 110 is connected to the electrosurgical generator 102, the switching mechanism switches the supply of RF energy to the monopolar plug. In embodiments, the electrosurgical generator 102 may be configured to provide RF energy to a plurality instruments simultaneously.

The electrosurgical generator 102 includes a user interface having suitable user controls (e.g., buttons, activators, switches, or touch screens) for providing control parameters to the electrosurgical generator 102. These controls allow the user to adjust parameters of the electrosurgical energy (e.g., the power level or the shape of the output waveform) so that the electrosurgical energy is suitable for a particular surgical procedure (e.g., coagulating, ablating, sealing, or cutting). The energy delivery devices 110 and 130 may also include a plurality of user controls. In addition, the electrosurgical generator 102 may include one or more display screens for displaying a variety of information related to operation of the electrosurgical generator 102 (e.g., intensity settings and treatment complete indicators).

Figure 2:
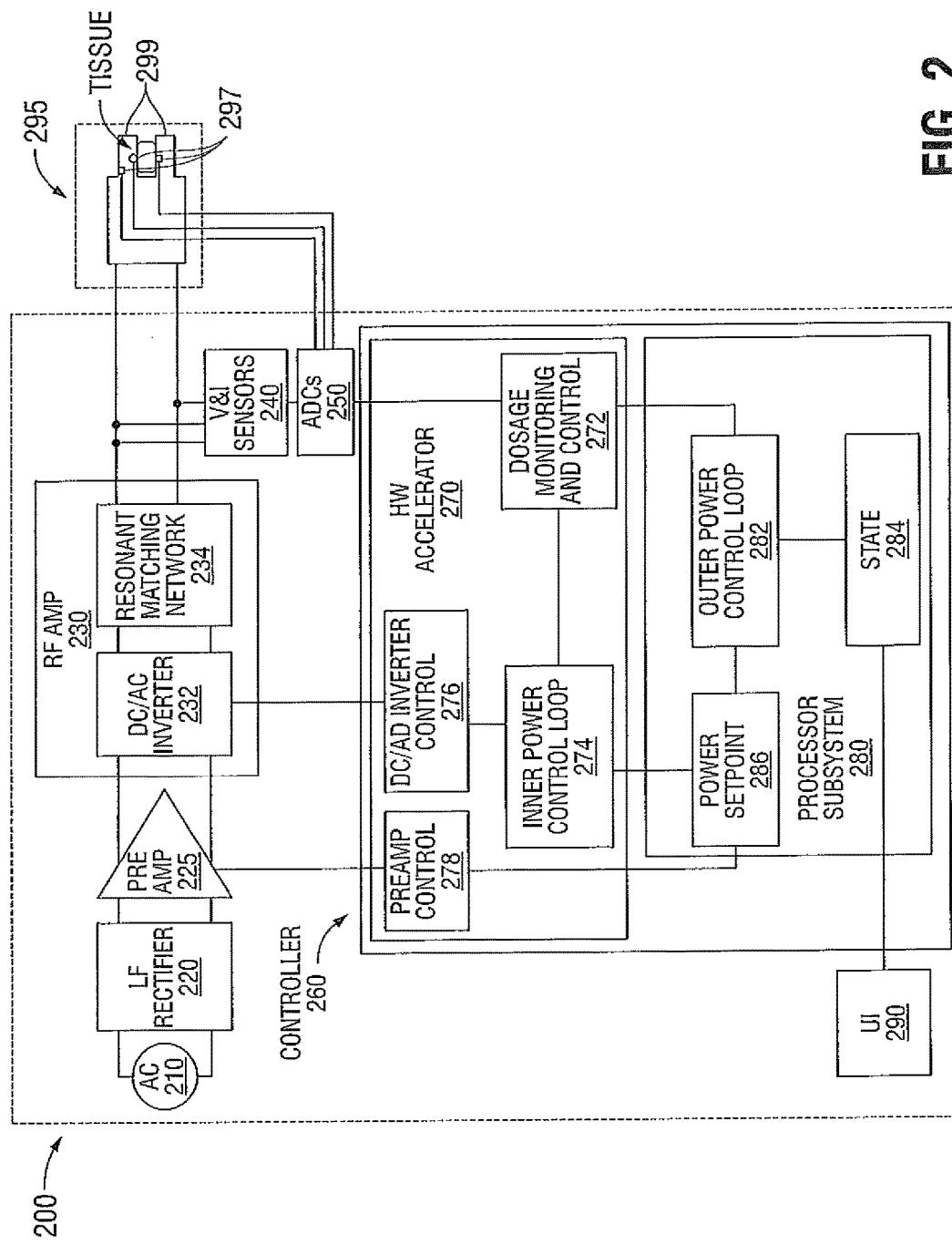
FIG. 2 is a block diagram of a generator circuitry of the electrosurgical generator of FIG. 1 and an energy delivery device connected to the generator circuitry.

FIG. 2 is a block diagram of generator circuitry 200 of the electrosurgical generator 102 of FIG. 1 and an energy delivery device 295 connected to the generator circuitry 200. The generator circuitry 200 includes a low frequency (LF) rectifier 220, a preamplifier 225, an RF amplifier 230, a plurality of sensors 240, analog-to-digital converters (ADCs) 250, a controller 260, a hardware accelerator 270, a processor subsystem 280, and a user interface (UI) 290. The electrosurgical generator 102 by way of the generator circuitry 200 is configured to connect to an alternating current (AC) power source 210, such as a wall power outlet or other power outlet, which generates AC having a low frequency (e.g., 25 Hz, 50 Hz, or 60 Hz). The AC power source 210 provides AC power to the LF rectifier 220, which converts the AC to direct current (DC).

The direct current (DC) output from the LF rectifier 220 is provided to the preamplifier 225 which amplifies the DC to a desired level. The amplified DC is provided to the RF amplifier 230, which includes a direct current-to-alternating current (DC/AC) inverter 232 and a resonant matching network 234. The DC/AC inverter 232 converts the amplified DC to an AC waveform having a frequency suitable for an electrosurgical procedure (e.g., 472 kHz, 29.5 kHz, and 19.7 kHz).

The appropriate frequency for the electrosurgical energy may differ based on electrosurgical procedures and modes of electrosurgery. For example, nerve and muscle stimulations cease at about 100,000 cycles per second (100 kHz) above which point some electrosurgical procedures can be performed safely; i.e., the electrosurgical energy can pass through a patient to targeted tissue with minimal neuromuscular stimulation. For example, typically ablation procedures use a frequency of 472 kHz. Other electrosurgical procedures can be performed at frequencies lower than 100 kHz, e.g., 29.5 kHz or 19.7 kHz, with minimal risk of damaging nerves and muscles. The DC/AC inverter 232 can output AC signals with various frequencies suitable for electrosurgical operations.

As described above, the RF amplifier 230 includes a resonant matching network 234. The resonant matching network 234 is coupled to the output of the DC/AC inverter 232 to match the impedance at the DC/AC inverter 232 to the impedance of the tissue so that there is maximum or optimal power transfer between the generator circuitry 200 and the tissue.

The electrosurgical energy provided by the DC/AC inverter 232 of the RF amplifier 230 is controlled by the controller 260. The voltage and current waveforms of the electrosurgical energy output from the DC/AC inverter 232 are sensed by the plurality of sensors 240 and provided to the controller 260, which generates control signals to control the output of the preamplifier 225 and the output of the DC/AC inverter 232. The controller 260 also receives input signals via the user interface (UI) 290. The UI 290 allows a user to select a type of electrosurgical procedure (e.g., monopolar or bipolar) and a mode (e.g., coagulation, ablation, sealing, or cutting), or input desired control parameters for the electrosurgical procedure or the mode.

The plurality of sensors 240 sense voltage and current at the output of the RF amplifier 230. The plurality of sensors 240 may include two or more pairs or sets of voltage and current sensors that provide redundant measurements of the voltage and current. This redundancy ensures the reliability, accuracy, and stability of the voltage and current measurements at the output of the RF amplifier 230. In embodiments, the plurality of sensors 240 may include fewer or more sets of voltage and current sensors depending on the application or the design requirements. The plurality of sensors 240 may measure the voltage and current output at the output of the RF amplifier 230 and from other components of the generator circuitry 200 such as the DC/AC inverter 232 or the resonant matching network 234. The plurality of sensors 240 that measures the voltage and current may include any known technology for measuring voltage and current including, for example, a Rogowski coil.

The DC/AC inverter 232 is electrically coupled to the energy delivery device 295 which may be a bipolar electrosurgical instrument 130 of FIG. 1, which has two jaw members to grasp and treat tissue with the energy provided by the DC/AC inverter 232.

The energy delivery device 295 includes temperature sensors 297 and two jaw members 299. An electrode is disposed on each of the two jaw members 299. The temperature sensors 297 may measure the temperatures of the tissue and the electrodes of the two jaw members 299. At least one of the temperature sensors 297 may be disposed on the energy delivery device 295 so that the at least one of the temperature sensors 297 can measure tissue temperature. At least another one of the temperature sensors 297 may be disposed on each jaw member of the bipolar electrosurgical instrument 130 in thermal communication with an electrode of each jaw member so that the temperatures of the jaw members can be measured. The temperature sensors 297 may employ any known technology for sensing or measuring temperature. For example, the temperature sensors 297 may include resistance temperature detectors, thermocouples, thermostats, thermistors, or any combination of these temperature sensing devices.

The sensed temperatures, voltage, and current are fed to analog-to-digital converters (ADCs) 250. The ADCs 250 sample the sensed temperatures, voltage, and current to obtain digital samples of the temperatures of the tissue and the jaw members and the voltage and current of the RF amplifier 230. The digital samples are processed by the controller 260 and used to generate a control signal to control the DC/AC inverter 232 of the RF amplifier 230 and the preamplifier 225. The ADCs 250 may be configured to sample outputs of the plurality of sensors 240 and the plurality of the temperature sensors 297 at a sampling frequency that is an integer multiple of the RF frequency.

As shown in FIG. 2, the controller 260 includes a hardware accelerator 270 and a processor subsystem 280. As described above, the controller 260 is also coupled to a UI 290, which receives input commands from a user and displays output and input information related to characteristics of the electrosurgical energy (e.g., selected power level). The hardware accelerator 270 processes the output from the ADCs 250 and cooperates with the processor subsystem 280 to generate control signals.

The hardware accelerator 270 includes a dosage monitoring and control (DMAC) 272, an inner power control loop 274, a DC/AC inverter controller 276, and a preamplifier controller 278. All or a portion of the controller 260 may be implemented by a field programmable gate array (FPGA), an application specific integrated circuit (ASIC), a digital signal processor (DSP), and/or a microcontroller.

The DMAC 272 receives samples of the temperatures of the tissue and the jaw members from the ADCs 250 and estimates a mass of the tissue and a thermal resistance scale factor between the tissue and the jaw members, as described in greater detail below. The DMAC 272 also calculates power of the energy provided to the tissue based on the sensed voltage and current. The DMAC 272 then provides the estimated mass of the tissue and the thermal resistance scale factor to the inner power control loop 274, which generates a control signal for the DC/AC inverter controller 276 based on the estimated mass and the estimated thermal resistance scale factor. The DC/AC inverter controller 276 in turn generates a first pulse-width modulation (PWM) control signal to control the output of the DC/AC inverter 232.

The processor subsystem 280 includes an outer power control loop 282, a state machine 284, and a power setpoint circuit 286. The processor subsystem 280 generates a second PWM control signal based on the output of the DMAC 272 and parameters (e.g., electrosurgical mode) selected by the user via the UI 290. Specifically, the parameters selected by the user are provided to the state machine 284 which determines a state or mode of the generator circuitry 200. The outer power control loop 282 uses this state information and the output from the DMAC 272 to determine control data. The control information is provided to the power setpoint circuit 286 which generates a power setpoint based on the control data. The preamplifier controller 278 uses the power setpoint to generate an appropriate PWM control signal for controlling the preamplifier 225 to amplify the DC output from the LF rectifier 220 to a desired level. If the user does not provide operational parameters to the state machine 284 via the UI 290, then the state machine 284 may maintain or enter a default state.

In other embodiments, the energy delivery device 295 may not include the temperature sensors 297. In those embodiments, the controller 260 of the generator circuitry 200 estimates changes in tissue impedance by using a forward difference equation or an equation relating temperature changes to changes in tissue impedance as described in more detail below.

Figure 3:
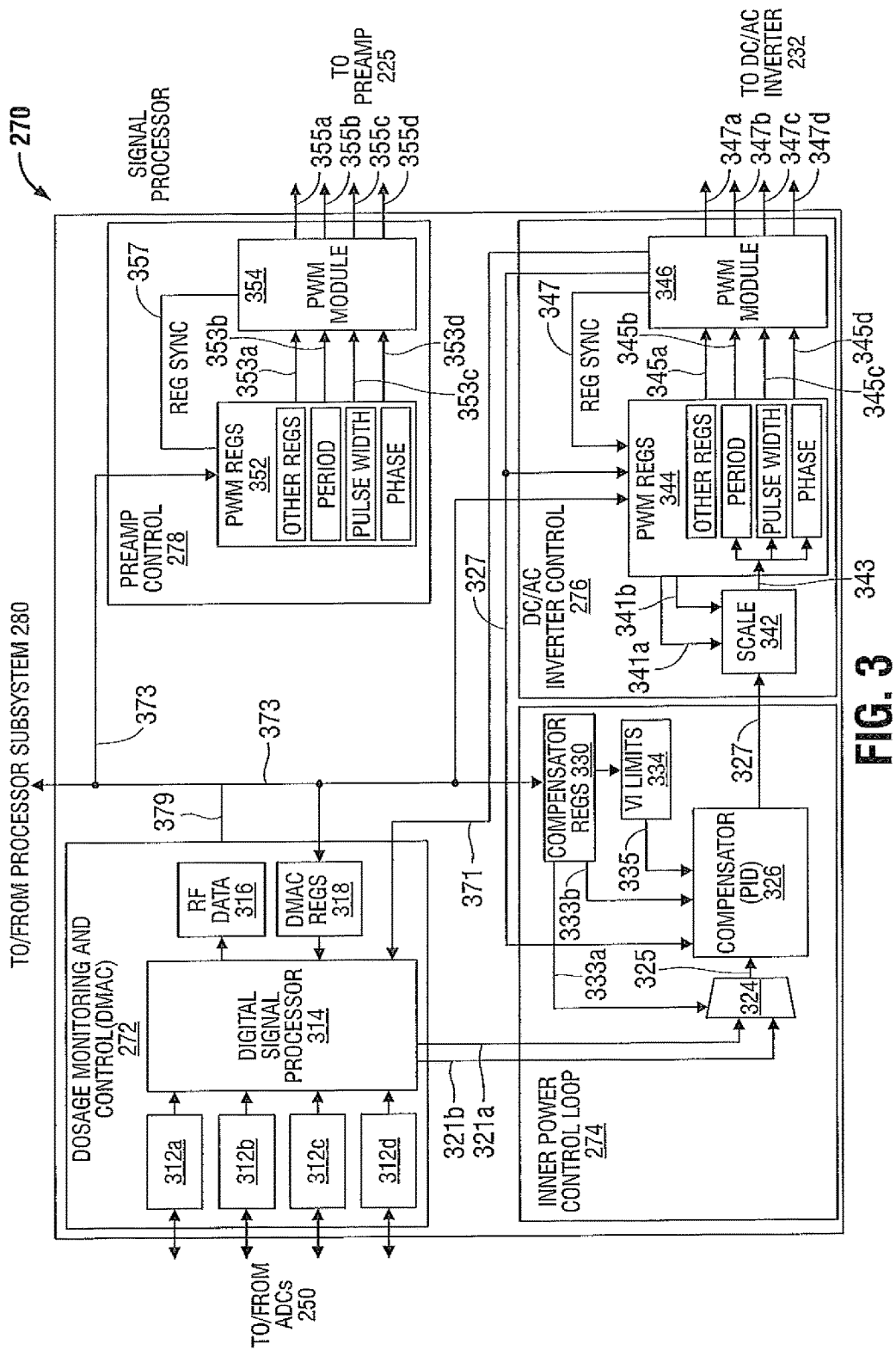
FIG. 3 is a schematic diagram of the controller of FIG. 2.

FIG. 3 shows a more detailed functional diagram of the hardware accelerator 270 of FIG. 2. The hardware accelerator 270 implements those functions of the generator circuitry 200 that may have special processing requirements such as high processing speeds. The hardware accelerator 270 includes the DMAC 272, the inner power control loop 274, the DC/AC inverter controller 276, and the preamplifier controller 278.

The DMAC 272 includes a plurality of analog-to-digital converter (ADC) controllers, e.g., four ADCs 312a-312d but not limited to this number, a digital signal processor 314, an RF data registers 316, and DMAC registers 318. The ADC controllers 312a-312d control the operation of the ADCs 250, which convert sensed temperatures, voltage, and current into digital data which is then provided to the digital signal processor 314 that implements digital signal processing functions, some of which are described in more detail below.

The sensed temperatures, voltage, and current are input to the ADCs 250, which sample the sensed temperatures, voltage, and current. The ADC controllers 312a-312d provide operational parameters, including a predetermined sampling rate, to the ADCs 250 so that the ADCs sample synchronously the temperatures of the tissue and the jaw members, the voltage, and the current at a predetermined sampling rate, i.e., a predetermined number of digital samples per second, or predetermined sampling period. The ADC controllers 312a-312d may be configured to control the ADCs 250 so that the sampling period corresponds to an integer multiple of the RF frequency of the electrosurgical energy.

The digital data obtained by sampling the sensed temperatures, voltage, and current is provided to the digital signal processor 314 via the ADC controllers 312a-312d. The digital signal processor 314 uses the digital data to estimate a mass of the tissue and a thermal resistance scale factor between the tissue and the jaw members. The estimation process is done by applying and combining physical principles and mathematical equations. Estimation process and derivation of relationship between the temperature and the mass of the tissue are explained in detail below.

The output of the digital signal processor 314 is provided to the processor subsystem 280 of FIG. 2 via RF data registers 316 and signal line 379. The DMAC 272 also includes DMAC registers 318 that receive and store relevant parameters for the digital signal processor 314. The digital signal processor 314 further receives signals from a PWM module 346 of the DC/AC inverter controller 276 via signal line 371.

The DMAC 272 provides control signals to the inner power control loop 274 via signal lines 321a and 321b and to the processor subsystem 280 via signal line 379. As shown in FIG. 2, the inner power control loop 274 processes the control signals and outputs a control signal to the DC/AC inverter controller 276. The inner power control loop 274 includes a multiplexer 324, a compensator 326, compensator registers 330, and VI limiter 334.

The multiplexer 324 receives the estimated mass of the tissue and the estimated thermal resistance scale factor via signal lines 321a and 321b. The multiplexer 324 also receives a select control signal, which selects one of the inputs from the compensator registers 330 via signal line 333a and provides the selected input to the compensator 326 via signal line 325. Thus, the digital signal processor 314 of the DMAC 272 generates control signals, which include the estimated mass and the estimated thermal resistance scale factor, and provides them to the multiplexer 324 of the inner power control loop 274 via the signal lines 321a and 321b, respectively.

When there is a user input, the processor subsystem 280 receives the user input and processes it with the outputs from the digital signal processor 314 via a signal line 379. The processor subsystem 280 provides control signals via a compensator registers 330 to a VI limiter 334, which corresponds to the power setpoint circuit 286 in FIG. 2. The VI limiter 334 then provides a desired power profile (e.g., a minimum and a maximum limits of the power for a set electrosurgical mode or operation) to the compensator 326 via signal line 335 based on the user input and the output of the digital signal processor 314, the compensator registers 330 also provide other control parameters to the compensator 326 via signal line 333b, and then the compensator 326 combines all control parameters from the compensator registers 330, the multiplexer 324, and the VI limiter 334 to generate output to the DC/AC inverter controller 276 via signal line 327.

The DC/AC inverter controller 276 receives a control parameter and outputs control signals that drives the DC/AC inverter 232. The DC/AC inverter controller 276 includes a scale unit 342, PWM registers 344, and the PWM module 346. The scale unit 342 scales the output of the compensator registers 330 by multiplying and/or adding a number to the output. The scale unit 342 receives a number for multiplication and/or a number for addition from the PWM registers 344 via signal lines 341a and 341b and provides its scaled result to the PWM registers 344 via signal line 343. The PWM registers 344 store several relevant parameters to control the DC/AC inverter 232, e.g., a period, a pulse width, and a phase of the AC signal to be generated by the DC/AC inverter 232 and other related parameters. The PWM module 346 receives output from the PWM registers 344 via signal lines 345a-345d and generates four control signals, 347a-347d, that control four transistors of the DC/AC inverter 232 of the RF amplifier 230 in FIG. 2. The PWM module 346 also synchronizes its information with the information in the PWM registers 344 via a register sync signal 347.

The PWM module 346 further provides control signals to the compensator 326 of the inner power control loop 274. The processor subsystem 280 provides control signals to the PWM module 346. In this way, the DC/AC inverter controller 276 can control the DC/AC inverter 232 of the RF amplifier 230 with integrated internal input (i.e., processed results from the plurality of sensors by the DMAC 272) and external input (i.e., processed results from the user input by the processor subsystem 280).

The processor subsystem 280 also sends the control signals to the preamplifier controller 278 via signal line 373. The preamplifier controller 278 processes the control signals and generates another control signal so that the preamplifier 225 amplifies direct current to a desired level suitable for being converted by the RF amplifier 230. The Preamplifier controller 278 includes PWM registers 352 and a PWM module 354. The PWM registers 352 receive outputs from the processor subsystem 280 via signal line 373, stores relevant parameters as the PWM registers 344 does, and provides the relevant parameters to the PWM module 354 via signal lines 353a-353d. The PWM module 354 also sends a register sync signal to the PWM registers 352 via signal line 357 and generates four control signals, 355a-355d, that control four transistors of the preamplifier 225 in FIG. 2.

Figure 4A:
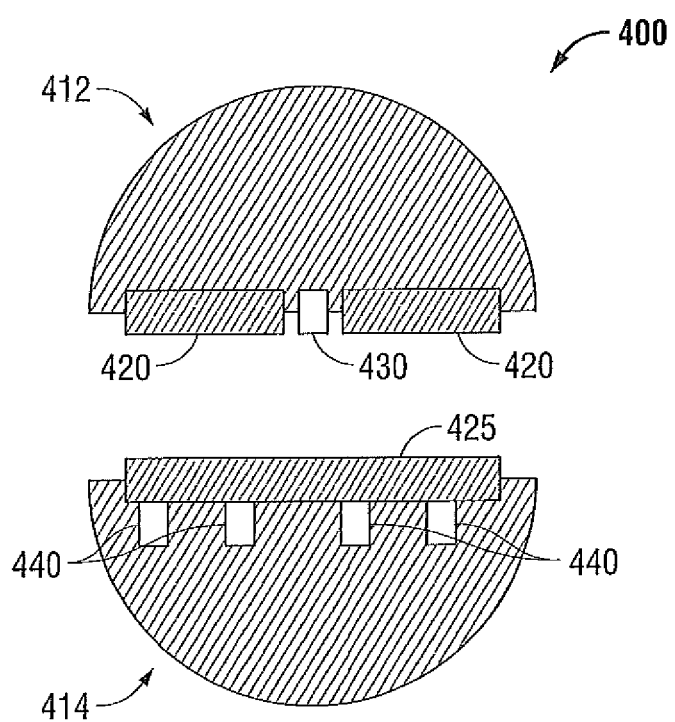
FIG. 4A is a front cross-sectional view of a jaw member assembly of an electrosurgical forceps of FIG. 1, which incorporates temperature sensors.

FIG. 4A shows a front cross-sectional view of a jaw member assembly 400 of the electrosurgical forceps of FIG. 1, which incorporate temperature sensors. The jaw member assembly 400 may form part of the energy delivery device 295 of FIG. 2. The jaw member assembly 400 includes jaw members 412, 414. Jaw member 412 includes active electrodes 420 for delivering electrosurgical energy to tissue, and a tissue temperature sensor 430 for sensing the temperature of tissue disposed between jaw members 412, 414. Jaw member 414 includes a return electrode 425 and a plurality of temperature sensors 440 for sensing the temperature of jaw member 414. Jaw members 412, 414 may be formed of insulating materials and are coupled to one another via a pivot (not shown) to permit movement of jaw members 412, 414 between an open position and an approximately closed position for grasping tissue between the jaw members 412, 414. The tissue temperature sensor 430 and the plurality of jaw member temperature sensors 440 are coupled to the controller 260 of the generator circuitry 200 and send signals representing sensed temperatures of the tissue and the jaw members to the ADCs 250 that sample the sensed temperature signals. A sampling rate of the sensed temperatures may be controlled by a portion of the ADC controllers 312a-312d of the DMAC 272. In this way, the controller 260 processes the digitally sampled temperatures of the tissue and the jaw members. The number of sensors of the tissue and of the plurality of sensors of the jaw members can be one or more based on the needs of the electrosurgery.

FIG. 4B shows a perspective view of a surgical stapler 450. The surgical stapler 450 includes a handle assembly 455 and an elongated body 460. A disposable loading unit 465 is releasably secured to a distal end of elongated body 460. Disposable loading unit 465 includes an end effector 470 having a staple cartridge assembly 472 housing a plurality of surgical staples (not shown) and an anvil 474 movably secured in relation to staple cartridge assembly 472 which is shown in expanded mode. Staple cartridge assembly 472 includes a tissue contacting surface 476 and anvil 474 includes a tissue contacting surface 478 juxtaposed to tissue contacting surface 476 of staple cartridge assembly 472.

Handle assembly 455 includes a stationary handle member 480, a movable handle member 482, and a barrel portion 484. A rotatable member 486 is preferably mounted on the forward end of barrel portion 484 to facilitate rotation of elongated body 460 with respect to handle assembly 455. An articulation lever 488 is also mounted on the forward end of the barrel portion 484 and adjacent to the rotatable member 486 to facilitate articulation of end effector 470.

The surgical stapler 450 may include a plurality of sensing devices 490 as shown in FIGS. 4B and 4C. For example, sensing devices 490 can be provided along the length of tissue contacting surface 478 of anvil 474, along the length of tissue contacting surface 476 of staple cartridge assembly 472, on disposable loading unit 465, on elongated body 460, and/or on handle assembly 455.

The sensing devices enable the measurement of various parameters of surgical stapler 450, such as temperatures of and temperature changes between tissue contacting surfaces 476 and 478 of surgical stapler 450. The sensed temperature and temperature changes may be used to estimate the mass of the tissue disposed between the tissue contacting surfaces 476 and 478. The estimated mass may then be used to determine the thickness or size of the tissue so that an operator of the stapler can properly configure the stapler, e.g., adjust the distance between the tissue contacting surfaces 476 and 478 or select a staple of suitable size.

As described above, the mass of the tissue and the thermal resistance scale factor (k) are estimated by modeling the temperatures of the tissue and the energy-based surgical device that is used to heat the tissue using a set or system of differential equations. This set of differential equations may be derived as follows. The temperature of the tissue increases when heat is added to the tissue, e.g., via electrical heating of the tissue, and the rate of change of the tissue temperature is related to the specific heat of the tissue. The following equation describes the relationship between the change in tissue temperature, the mass of the tissue, and the added heat:

$$\frac{d}{dt}T = \frac{\frac{d}{dt}Q}{C_p M}, \tag{1}$$

where $$\frac{d}{dt}T$$

represents the change in tissue temperature with respect to time, $$\frac{d}{dt}Q$$

represents the heat added to the tissue in joules with respect to time, $C_p$ is the specific heat in joules/kg, and M is the mass of the tissue in kg. Equation (1) may be rewritten as:

$$dT = \frac{dQ}{C_p M} \tag{2}$$

where dT represents the change in temperature and dQ represents the heat added to the tissue. In other words, the change in temperature dT is the ratio between the heat added to the tissue dQ and the product of the specific heat $C_p$ and the mass M of the tissue.

The conduction of heat through tissue depends on the water content in the tissue and the mobility of ions in the tissue caused by the conduction of electrical energy. This relationship is given by the following equation:

$$\sigma = \sigma_0 \frac{W}{W_0} e^{\alpha(T-T_0)}, \tag{3}$$

where σ is the current electrical conductivity in Siemens per meter (S/m), $\sigma_0$ is the initial conductivity of the tissue in S/m, W is the current water content of the tissue in kg or kg/m³, $W_0$ is the initial water content of the tissue in kg or kg/m³, α is a unitless temperature coefficient constant of ion mobility, T is the current temperature in Kelvin, and $T_0$ is the initial temperature in Kelvin which corresponds to $\sigma_0$ and $W_0$. Equation (3) can be solved for the temperature change, i.e., $dT = T - T_0$, yielding the following equation:

$$dT = \frac{1}{\alpha} \ln\left(\frac{W_0 \sigma}{W \sigma_0}\right). \tag{4}$$

The tissue impedance may be expressed as a function of conductivity by the following equation:

$$Z = \frac{1}{\sigma} \cdot \frac{L}{A}, \tag{5}$$

where Z is the current impedance in ohms, σ is the current conductivity of the tissue in S/m, L is the length of the tissue grasped by the jaw members in meters (m), A is the area of the tissue grasped by the jaw members in square meters (m²). The starting impedance may similarly be expressed by the following equation:

$$Z = \frac{1}{\sigma_0} \cdot \frac{L}{A}, \qquad (6)$$

where $Z_0$ is the starting impedance in ohms and $\sigma_0$ is the starting conductivity of the tissue in S/m. Combining equations (3)-(5) results in the following equation:

$$dT = \frac{1}{\alpha} \ln\left(\frac{W_0 Z_0}{WZ}\right). \qquad (7)$$

A thermal resistance scale factor k between the tissue and the jaw members of the energy-based medical device may be incorporated into equation (7) to accommodate different ratios of heat conductivity between the tissue and the jaw members of the energy-based medical device. Thus, after incorporating the thermal resistance scale factor k, equation (7) becomes:

$$dT = \frac{k}{\alpha} \ln\left(\frac{W_0 Z_0}{WZ}\right). \qquad (8)$$

Equation (8) is an accurate estimate of the temperature change at the start of a sealing or ablation procedure. However, equation (8) may not be as accurate thereafter. For example, as the jaw members of the energy delivery device transfers electrical energy to the tissue, the electrical energy is converted into heat due to the thermal resistance of the tissue and the temperature of the tissue rises. As the temperature of the tissue rises, water in the tissue starts to vaporize into the environment. Equation (8) is not accurate in this situation because equation (8) assumes that there is no water loss from the tissue and thus no change in impedance.

When water loss starts to occur, the tissue temperature does not change until most of water in the tissue is vaporized. Thus, equation (8) may not be accurate in this situation either. However, assuming that the water content of the tissue to be treated is very small and vaporization of water is also negligible, equation (8) can be expressed as follows:

$$dT = \frac{k}{\alpha} \ln\left(\frac{Z_0}{Z}\right) \qquad (9)$$

Equation (9) shows that the change in tissue temperature is dependent upon change in impedance assuming that there is negligible water loss. Thus, equation (9) may be used to determine changes in tissue temperature based upon measurements of the tissue impedance (i.e., measurements of $Z_0$ and Z) due to a pulse of RF energy applied to the tissue. The current impedance can be obtained by solving equation (9) for Z, which results in the following equation:

$$Z = Z_0 \cdot e^{-\frac{\alpha dT}{k}}. \qquad (10)$$

The mass of the tissue M may be obtained by combining equations (2) and (9) and solving the combined equations for M, as follows:

$$\frac{dQ}{C_p M} = \frac{k}{\alpha} \ln\left(\frac{Z_0}{Z}\right) \Rightarrow M = \frac{\alpha dQ}{C_p k \ln\left(\frac{Z_0}{Z}\right)}. \qquad (11)$$

Again, equation (11) assumes that water content of the tissue to be treated is very small and that the loss of water, i.e., the vaporization of water, is also negligible. Equation (11) does not contemplate energy loss between the tissue and the jaw members of the energy-based medical device and, thus, is not sufficient to model the temperature change between the tissue and the jaw members of the energy-based medical device during a sealing or ablation procedure.

Assuming that the mass and the thermal resistance scale factor are known or estimated, temperatures of the tissue or the jaw members of the energy-based medical device can be modeled by using heat-related equations. According to the Newton's law of cooling, the heat loss from the tissue depends on the temperature difference between the tissue and the jaw members of an energy-based medical device, which is represented by the equation:

$$\frac{d}{dt} T_t = -k(T_t(t) - T_j(t)), \qquad (12)$$

where $T_t(t)$ is the tissue temperature (the subscript t refers to tissue), $T_j(t)$ is the temperature of the jaw members (the subscript j refers to jaw members), and k is a thermal resistance scale factor which is $$\frac{hA}{C_p M}$$

between the tissue and the jaw members, where h is a heat transfer coefficient, A is the surface area of the jaw member which is in contact with tissue, $C_p$ is specific heat, and M is the mass of the tissue grasped by the jaw members. Additionally, the change in the tissue temperature depends on the change of heat added and lost to the jaw members, which is represented by the following equation:

$$\frac{d}{dt} T_t = \frac{\frac{d}{dt} Q_{add}(t) + \frac{d}{dt} Q_{loss}(t)}{C_{p_t} M_t}. \qquad (13)$$

Equation (13) is another way to represent equation (2). In some embodiments, the energy-based medical device may be configured to minimize heat loss from the tissue to the jaw members using equation (13). Thus, assuming that heat loss is minimized and further assuming that heat loss to the environment is considered negligible, equation (13) becomes:

$$\frac{d}{dt} T_t = \frac{\frac{d}{dt} Q_{add}(t)}{C_{p_t} M_t}. \qquad (14)$$

The basic temperature difference equations of the tissue and of the jaw members may be obtained by combining equations (12) and (13) as follows:

$$\frac{d}{dt}T_t = -k(T_t(t) - T_j(t)) + \frac{\frac{d}{dt}Q_{add}(t)}{C_{P_t}M_t}, \text{ or} \quad (15)$$

$$T_j = T_t(t) + \frac{\frac{d}{dt}T_t(t)}{k} - \frac{\frac{d}{dt}Q_{add}(t)}{kC_{P_t}M_t}. \quad (16)$$

The temperature change ratio of the jaw members depends on the temperature change between the tissue temperature and the jaw members' temperature. Even though the jaw members are exposed to the environment, heat added from and lost to the environment is assumed to be negligible because of insulation of the jaw member assembly 400 and the large mass of the jaw members as compared to the tissue. Thus, the mathematical term representing the heat added to the environment can be ignored or considered as 0. As a result, the basic temperature difference equation of the jaw members is:

$$\frac{d}{dt}T_j = k(T_t(t) - T_j(t)). \quad (17)$$

Applying equation (16) to equation (17) eliminates the term $T_j$ and results in the following equation for the tissue:

$$\frac{d}{dt}\left(T_t(t) + \frac{\frac{d}{dt}T_t(t)}{k} - \frac{\frac{d}{dt}Q_{add}(t)}{kC_{P_t}M_t}\right) = k\left(T_t(t) - \left(T_t(t) + \frac{\frac{d}{dt}T_t(t)}{k} - \frac{\frac{d}{dt}Q_{add}(t)}{kC_{P_t}M_t}\right)\right) \quad (18)$$

A simplified version of equation (18) may be expressed in the form of a second-order differential equation, which is given by:

$$\frac{d^2}{dt^2}T_t(t) + 2k\frac{d}{dt}T_t(t) = \frac{\frac{d^2}{dt^2}Q_{add}(t) + k\frac{d}{dt}Q_{add}(t)}{C_{P_t}M_t}. \quad (19)$$

In a similar way, equation (17) may be applied to equation (16) to eliminate the term $T_t$ and the resulting equation may be simply expressed in the form a second order differential equation given by:

$$\frac{d^2}{dt^2}T_j(t) + 2k\frac{d}{dt}T_j(t) = \frac{k\frac{d}{dt}Q_{add}(t)}{C_{P_t}M_t}. \quad (20)$$

Equations (19) and (20) may be used to predict temperatures of the jaw members and the tissue, respectively. Since the rate of heat change is a form of power, i.e., $$\frac{d}{dt}Q(t) = Pwr(t),$$

equations (19) and (20) can also be written as:

$$\frac{d^2}{dt^2}T_j(t) + 2k\frac{d}{dt}T_j(t) = \frac{kPwr(t)}{C_{P_t}M_t} \quad (21)$$

and $$\frac{d^2}{dt^2}T_j(t) + 2k\frac{d}{dt}T_j(t) = \frac{kPwr(t)}{C_{P_t}M_t}, \quad (22)$$

where Pwr(t) is the power that may be any forcing function, such as a step response, exponential, sinusoid, single pulse, two pulses, or any other suitable signal for sealing and ablation procedures. The power is controlled by the controller 260 of the generator circuitry 200. The plurality of sensors 240 sense the voltage and current at the output of the RF Amp 230 and the DMAC 272 calculates power by multiplying the voltage and current of in any suitable ways.

Equations (21) and (22) are second-order differential equations that may be used to predict the temperatures of the tissue and the jaw members based upon a known thermal resistance scale factor and a known mass of the jaw members. Conversely, equations (21) and (22) may be used to estimate the thermal resistance scale factor and the mass of the tissue based upon known or measured temperatures of the tissue and jaw members.

The solution to the system of second-order differential equations given by equations (21) and (22) is:

$$T_t(t) = \frac{P - e^{-2 \cdot k \cdot t}P + 2P \cdot k \cdot t + 2C_{P_t}M_t T_{j_0}k + 2C_{P_t}M_t T_{t_0}k - 2e^{-2 \cdot k \cdot t}C_{P_t}M_t T_{j_0}k + 2e^{-2 \cdot k \cdot t}C_{P_t}M_t T_{t_0}k}{4C_{P_t}M_t k} \quad (23)$$

and $$T_j(t) = \frac{e^{-2 \cdot k \cdot t}P - P + 2P \cdot k \cdot t + 2C_{P_t}M_t T_{j_0}k + 2C_{P_t}M_t T_{t_0}k + 2e^{-2 \cdot k \cdot t}C_{P_t}M_t T_{j_0}k - 2e^{-2 \cdot k \cdot t}C_{P_t}M_t T_{t_0}k}{4C_{P_t}M_t k}, \quad (24)$$

where $T_{t_0}$ and $T_{j_0}$ are the initial temperatures of the tissue and the jaw members, respectively, and P is the power level Pwr(t).

Assuming that the initial temperatures of the tissue and the jaw members are zero, equations (23) and (24) become:

$$T_t(t) = \frac{P - e^{-2 \cdot k \cdot t}P + 2P \cdot k \cdot t}{4C_{P_t}M_t k} = \frac{P \cdot t}{2C_{P_t}M_t} + \frac{P}{4C_{P_t}M_t k} - \frac{Pe^{-2 \cdot k \cdot t}}{4C_{P_t}M_t k} \quad (25)$$

and $$T_j(t) = \frac{e^{-2 \cdot k \cdot t}P - P + 2P \cdot k \cdot t}{4C_{P_t}M_t k} = \frac{P \cdot t}{2C_{P_t}M_t} - \frac{P}{4C_{P_t}M_t k} + \frac{Pe^{-2 \cdot k \cdot t}}{4C_{P_t}M_t k} \quad (26)$$

The rate of change in tissue temperature is determined by taking the derivative of equation (25) with respect to time, which results in the equation:

$$\frac{d}{dt}T_t(t) = \frac{e^{-2 \cdot k \cdot t}P + P}{2C_{P_t}M_t} = \frac{P}{2C_{P_t}M_t} + \frac{Pe^{-2 \cdot k \cdot t}}{2C_{P_t}M_t} \quad (27)$$

After the method 500 starts, an index i is initialized to zero in step 505 and is incremented by one in step 510. In step 515, the controller 260 causes the generator circuitry 200 to supply electrosurgical energy, e.g., alternating current, at a desired power level to the tissue to be treated via the jaw members of an electrosurgical instrument coupled to the generator. The electrosurgical energy causes the temperature of the tissue to rise. As the temperature of the tissue rises, heat is transferred from the tissue to the jaw members, which causes the temperature of the jaw members to rise. Since the parameters of the jaw members are known, temperature changes in the jaw members can be calculated by using equation (26).

Figure 5:
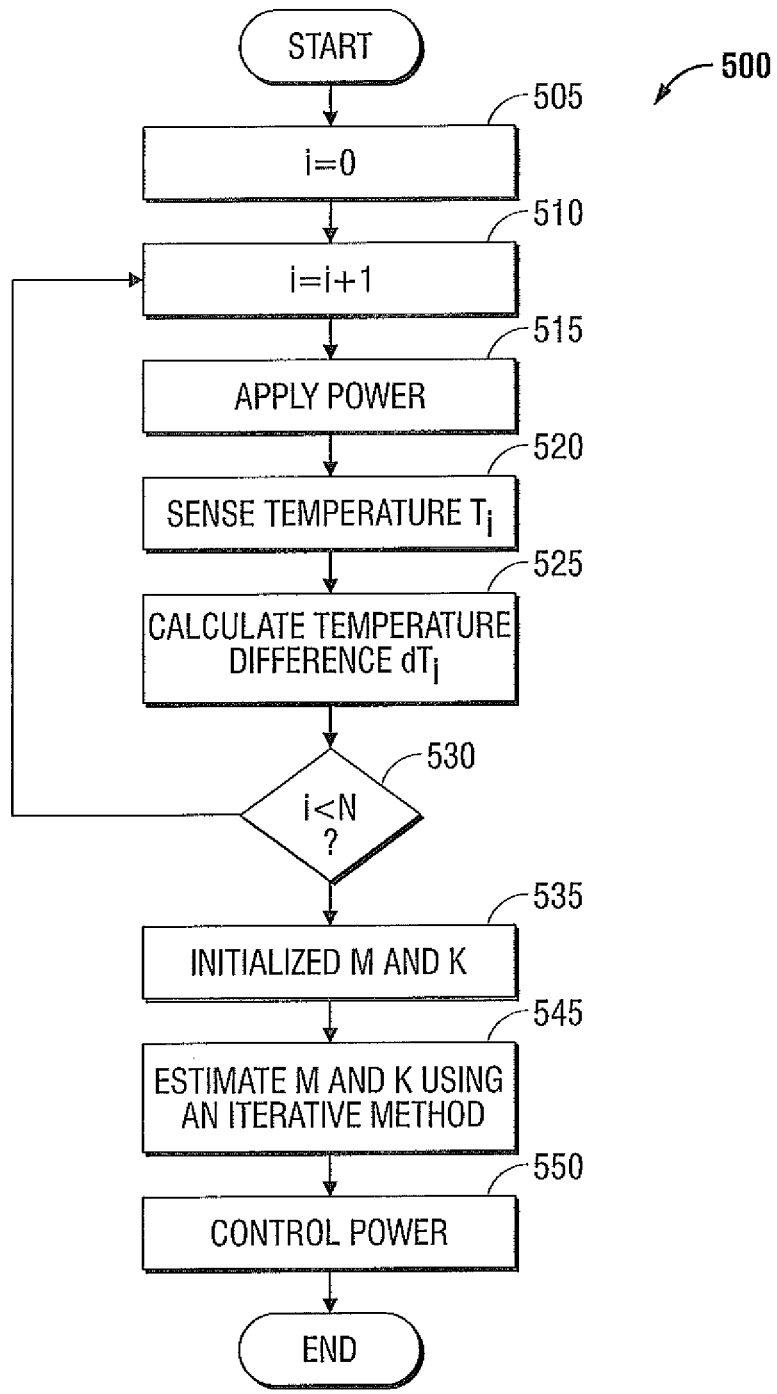
FIG. 5 is a flow diagram illustrating a method of estimating tissue mass and the thermal resistance scale factor that may be performed by the digital signal processor of FIG. 2 in accordance with some embodiments of the present disclosure.

Various iterative and non-iterative methods may be employed to estimate the thermal resistance scale factor and the mass of tissue using equations (25) and (27). FIG. 5 illustrates a method 500 for estimating the thermal resistance scale factor and the mass of tissue using an iterative gradient descent algorithm. The method 500 utilizes equations (25) and (27) in a discrete sense. In particular, the method 500 uses a change in temperature or a temperature difference $dT_i(t)$ rather than a derivative of the temperature $$\frac{d}{dt} T_i(t)$$

for each iteration.

In the case of measuring the thermal resistance scale factor and the mass of tissue, the temperature $T_i$ of the tissue is sensed by a plurality of temperature sensors 297 in step 520. In step 525, a temperature difference $dT_i$, which is equal to the difference between the current tissue temperature $T_i$ and the previous tissue temperature $T_{i-1}$, is calculated. When the index i is equal to one, $dT_i$ is zero, and when the index i is greater than one, $dT_i$ is equal to the difference between current tissue temperature $T_i$ and the previous tissue temperature $T_{i-1}$.

In embodiments, the temperature difference $dT_i$ may be determined based on changes in measured or estimated tissue impedance. In this case, the method 500 may first estimate tissue impedance after applying power to the tissue in step 510 and then may estimate temperature changes $dT_i$ based on changes in the estimated tissue impedance by using equation (9).

In step 530, the index i is compared to the number of desired iterations N. If the index i is less than the number of iterations N, steps 510 to 525 are repeated. If the index i is equal to N, the mass M and the thermal resistance scale factor K are initialized in step 535 and then estimated using an iterative method in step 545.

Figure 6A:
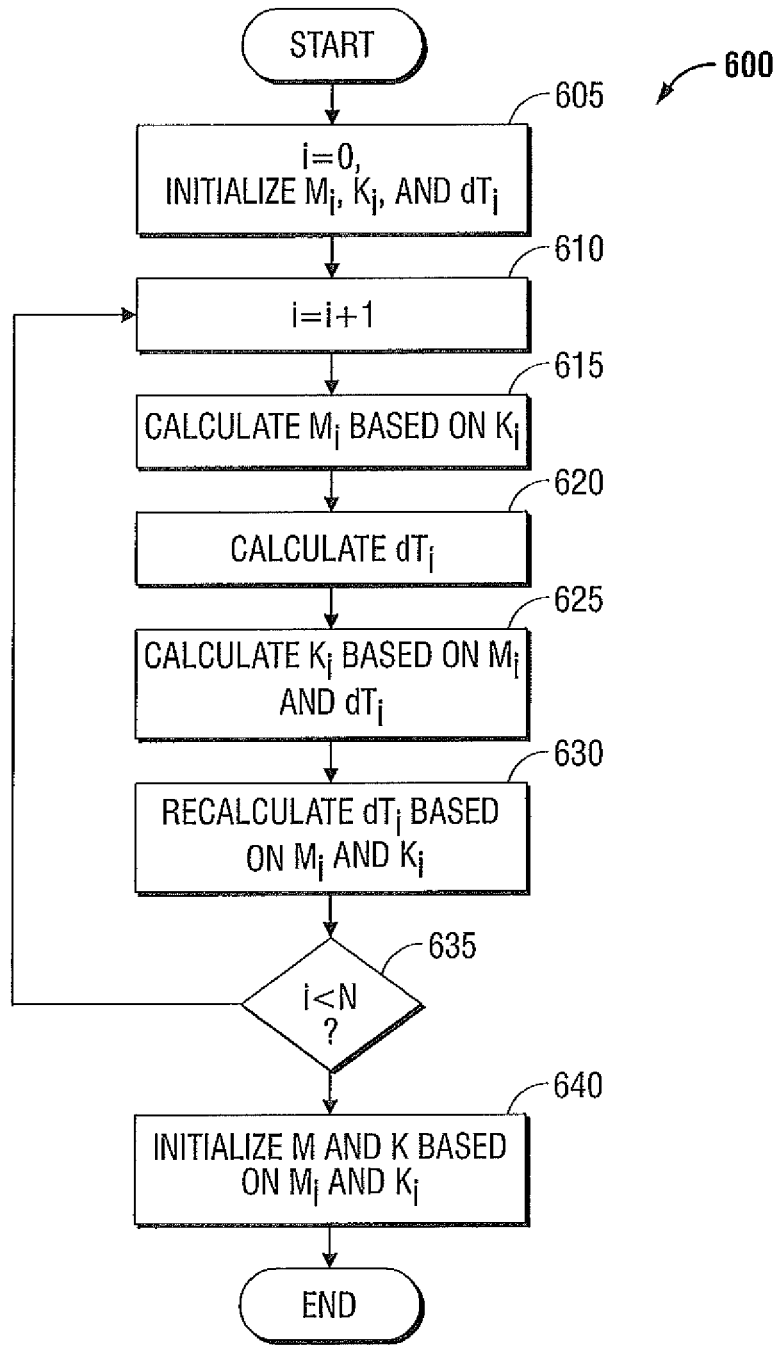
FIGS. 6A-6D are flow diagrams illustrating a gradient descent method of estimating tissue mass and the thermal resistance scale factor in accordance with further embodiments of the present disclosure.
Figure 6B:
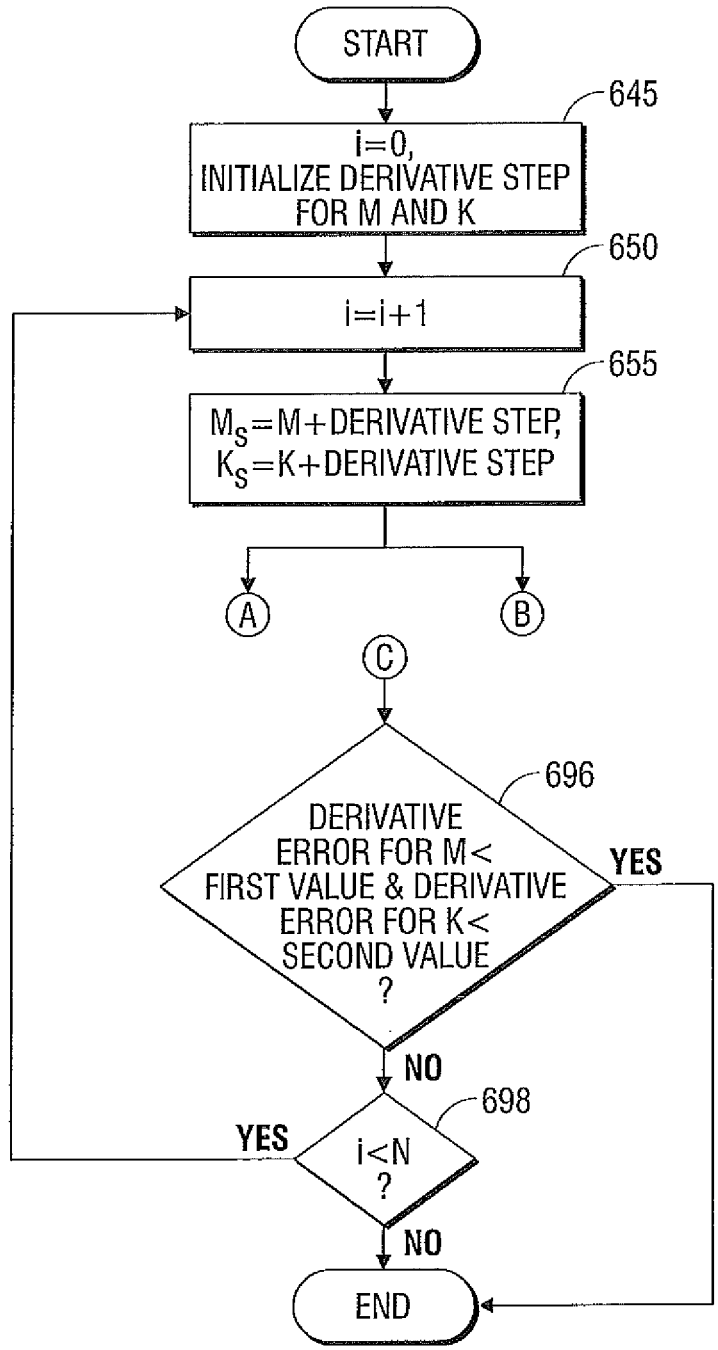
Figure 6C:
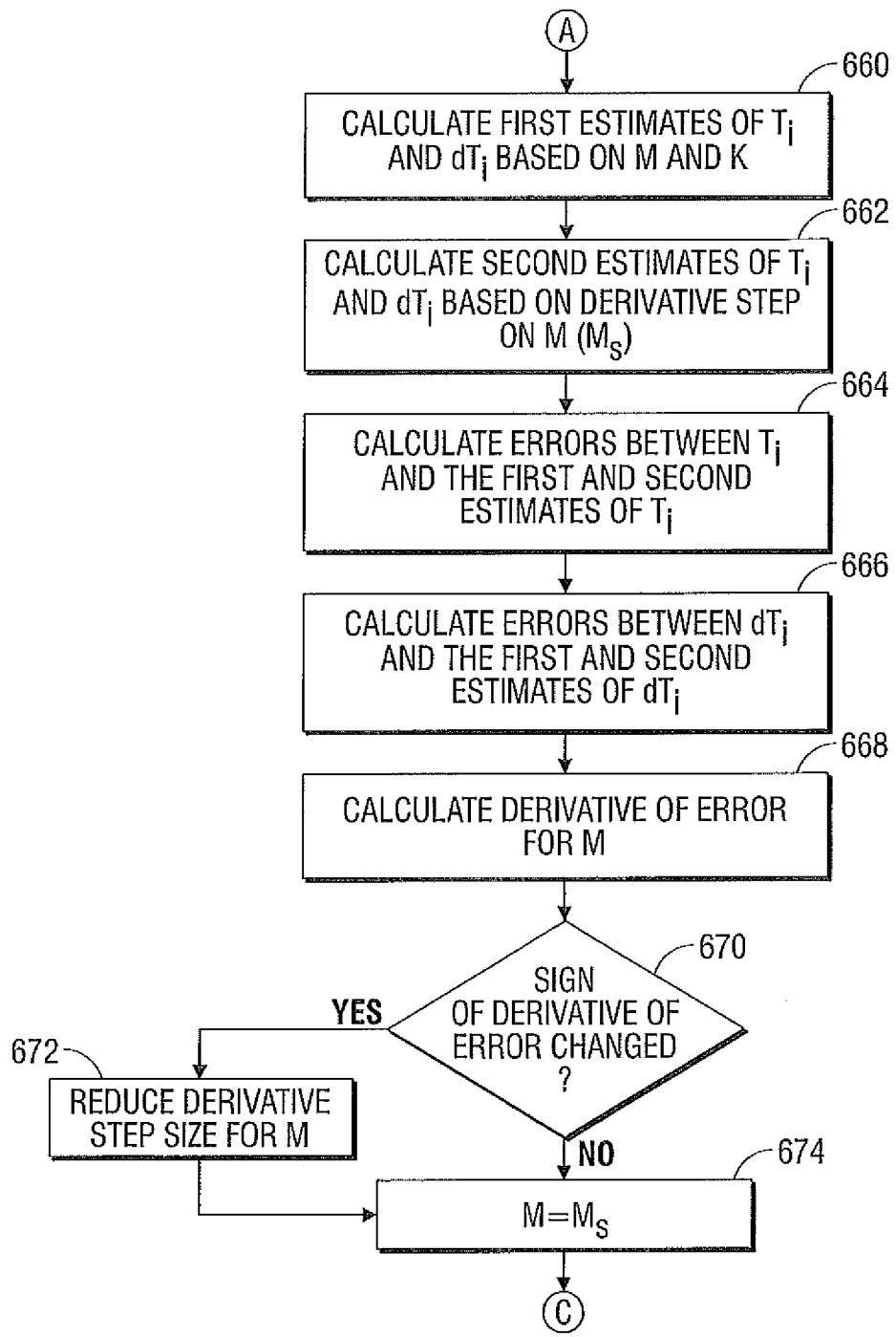
Figure 6D:
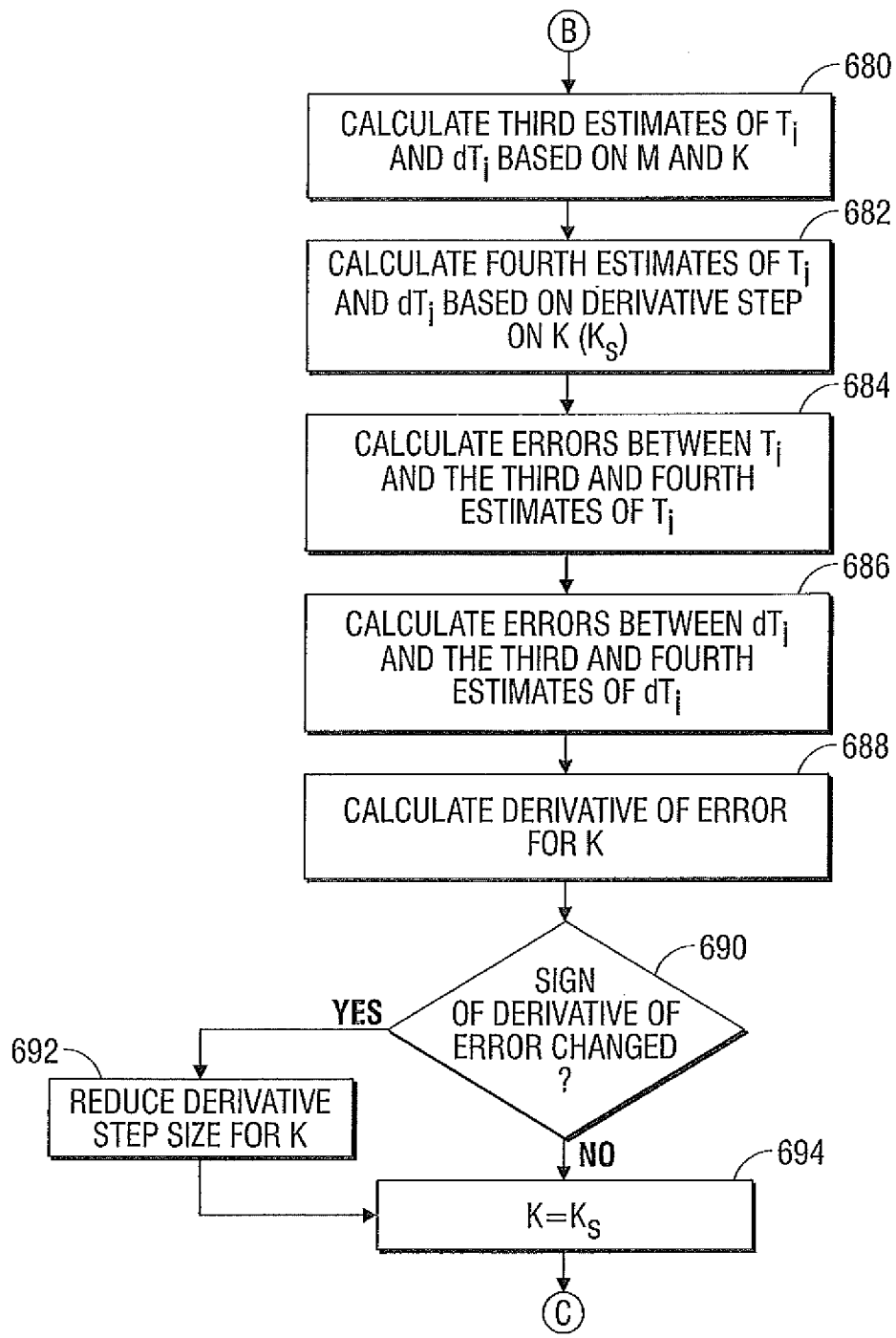

In step 545, the true mass and the true thermal resistance scale factor are estimated by using gradient descent which adjusts a derivative step of the mass and thermal resistance scale factor based on errors and is described in more detail in FIGS. 6B-6D. Afterwards, the controller 260 controls levels of power to adjust the temperature of the tissue and the jaw members during electrosurgery based on the estimates of the mass and the thermal resistance scale factor in step 550.

FIG. 6A is a flow diagram of a method 600 of determining starting estimates of the mass and the thermal resistance scale factor for the gradient descent method. After starting, an index i is initialized to zero in step 605. Also, an array of masses $M_i$ and thermal resistance scale factors $K_i$ corresponding to measured temperatures $T_i$ are set to non-zero values, and an array of temperature differences $dT_i$ are set to zero in step 605.

In step 610, the index i is incremented by one. In step 615, an estimate of the mass $M_i$ is calculated based on the thermal resistance scale factor $K_i$ using the following equation:

$$M_i = \frac{P + 2P \cdot K_i \cdot t_i - P \cdot e^{-2 \cdot K_i \cdot t_i}}{4 C_p K_i T_i}, \quad (31)$$

where P is the power level, $K_i$ is the thermal resistance scale factor at index i, $t_i$ is time in seconds at index i, $C_p$ is the specific heat constant for tissue, and $T_i$ is the sensed temperature at index i. Equation (31) is derived from equation (25) by solving for the mass M. In step 620, the temperature difference $dT_i$ at index i is calculated according to the following equation:

$$dT_i = \frac{e^{-2 \cdot K_i \cdot t_i} P + P}{2 C_p M_i}, \quad (32)$$

which is the discretized version of equation (27).

In step 625, an estimate of the thermal resistance scale factor $K_i$ is calculated based on the previously calculated mass $M_i$ and the temperature difference $dT_i$ using the following equation:

$$K_i = \frac{-\ln\left(\frac{2 C_p M_i dT_i - P}{P}\right)}{2t}, \quad (33)$$

which is derived from equation (32) by solving for thermal resistance scale factor $K_i$. Next, in step 630, the temperature difference $dT_i$ is recalculated based on the estimates of the mass $M_i$ and the thermal resistance scale factor $K_i$.

In step 635, the index i is compared to a predetermined number N, which is the length of the array of samples of the tissue temperature $T_i$. If it is determined that the index i is less the predetermined number N, steps 610 through 630 are repeated. Otherwise, in step 640, an estimated starting mass M and starting thermal resistance scale factor K are set for the gradient descent algorithm based on the masses $M_i$ and the thermal resistance scale factors $K_i$. For example, the maximum of the array of masses $M_i$ and the maximum of the array of thermal resistance scale factors $K_i$ may be set as the estimated starting mass M and the estimated starting thermal resistance scale factor estimate K, respectively. Alternatively, the minimum of the array of masses $M_i$ and the maximum of the array of thermal resistance scale factors $K_i$ may be set as the estimated starting mass M and the estimated starting thermal resistance scale factor K, respectively. In a further alternative, the average of the array of masses $M_i$ and the average of the array of thermal resistance scale factor $K_i$ may be set as the estimated starting mass M and the estimated starting thermal resistance scale factor K for the gradient descent algorithm.

FIGS. 6B-6D are flow diagrams illustrating the gradient descent method that estimates the mass M and the thermal resistance scale factor K according to embodiments of the present disclosure. As shown in FIG. 6B, in step 645, an index i is initialized to zero, a derivative step for the estimated mass is initialized to a non-zero value, e.g., $1 \times 10^{-7}$, and a derivative step for the estimated thermal resistance scale factor is initialized to a non-zero value, e.g., 1.0. According to the gradient descent algorithm, the derivative step for the mass estimate is used to increase or decrease the mass estimate so that the mass estimate reaches a value close to the actual value, and the derivative step for the estimated thermal resistance scale factor is used to increase or decrease the estimated thermal resistance scale factor so that the estimated thermal resistance scale factor reaches a value close to the actual value. In step 650, the index i is incremented until the index reaches a predetermined number N.

In step 655, a second mass estimate $M_s$ is calculated by summing the starting or first mass estimate M and the derivative step for the mass and a second thermal resistance scale factor $K_s$ is calculated by summing the starting or first thermal resistance scale factor estimate K and the derivative step for the thermal resistance scale factor.

FIG. 6C shows a flow diagram that continues from the flow diagram of FIG. 6B for determining the mass estimate according to the gradient descent method. In step 660, first estimates for the temperature and the temperature difference are calculated according to the following forward difference equations:

$$\hat{T}_i = \frac{P - e^{-2 \cdot K \cdot t_i} P + 2P \cdot K \cdot t_i}{4 C_p M K}, \text{ and} \quad (34)$$

$$d\hat{T}_i = \frac{e^{-2 \cdot K \cdot t_i} P + P}{2 C_p M}, \quad (35)$$

where M is the first mass estimate. In step 662, a second estimate of the temperature and the temperature difference, $\hat{T}s_i$ and $d\hat{T}s_i$, are calculated based on the second mass estimate $M_s$ using equations (34) and (35).

Next, in step 664, a first temperature error between the sensed temperature $T_i$ and the first estimated temperature $\hat{T}_i$ is calculated, and a second temperature error between the sensed temperature $T_i$ and the second estimated temperature $\hat{T}s_i$ is calculated. Similarly, in step 666, a first temperature difference error between the sensed temperature difference $dT_i$ and the first estimated temperature difference $d\hat{T}_i$ is calculated, and a second temperature difference error between the sensed temperature difference $dT_i$ and the second estimated temperature difference $d\hat{T}s_i$ is calculated.

In step 668, a derivative of the error is calculated. The derivative of the error may be calculated by finding the difference between the sum of the first errors and the sum of the second errors and dividing the resulting difference by the sum of the first errors.

In step 670, simulated annealing is performed by first determining whether the sign of the derivative of the error has changed. If the sign of the derivative of the error has changed, the derivative step size is reduced in step 672 and the first estimated mass is set equal to the second estimated mass. If the sign of the derivative of the error has not changed, the first estimated mass is set equal to the second estimated mass. The simulated annealing process reduces the derivative step size as the error approaches a predetermined value to prevent the iterative method from oscillating when the derivative step size is too large.

FIG. 6D shows a flow diagram that continues from the flow diagram of FIG. 6B for determining the thermal resistance scale factor estimate according to the gradient descent method. In step 680, third estimates for the temperature and the temperature difference are calculated according to equations (34) and (35) where K is the first thermal resistance scale factor estimate. In step 682, a fourth estimate of the temperature and the temperature difference, $\hat{T}s_i$ and $d\hat{T}s_i$, are calculated based on the second thermal resistance scale factor estimate $K_s$ using equations (34) and (35).

Next, in step 684, a third temperature error between the sensed temperature $T_i$ and the third estimated temperature $\hat{T}_i$ is calculated, and a fourth temperature error between the sensed temperature $T_i$ and the fourth estimated temperature $\hat{T}s_i$ is calculated. Similarly, in step 686, a third temperature difference error between the sensed temperature difference $dT_i$ and the third estimated temperature difference $d\hat{T}_i$ is calculated, and a fourth temperature difference error between the sensed temperature difference $dT_i$ and the fourth estimated temperature difference $d\hat{T}s_i$ is calculated.

In step 688, a derivative of the error is calculated. The derivative of the error may be calculated by finding the difference between the sum of the third errors and the sum of the fourth errors and dividing the resulting difference by the sum of the third errors.

In step 690, simulated annealing is performed by first determining whether the sign of the derivative of the error has changed. If the sign of the derivative of the error has changed, the derivative step size is reduced in step 692 and the first estimated thermal resistance scale factor K is set equal to the second estimated thermal resistance scale factor $K_s$. If the sign of the derivative of the error has not changed, the first estimated thermal resistance scale factor K is set equal to the second estimated thermal resistance scale factor $K_s$ in step 694.

After step 674 and 694 of FIGS. 6C and 6D, respectively, are performed, it is determined whether the derivative error for the mass estimate M is less than a first threshold value and the derivative error for the thermal resistance scale factor estimate K is less than a second threshold value in step 696. If it is determined that the derivative errors for M and K are less than respective first and second threshold values, the gradient descent method is ended because the estimates of the mass and thermal resistance scale factor are deemed to be sufficiently close to the actual mass and thermal resistance scale factor. Otherwise, the index i is compared with the predetermined number N in step 698. If the index i is less than the predetermined number N, the gradient descent method returns to step 650 and all steps from 650 to 698 in FIGS. 6B-6D are repeated until the index i reaches the predetermined number N or until the conditions described in step 696 are met.

Figure 7:
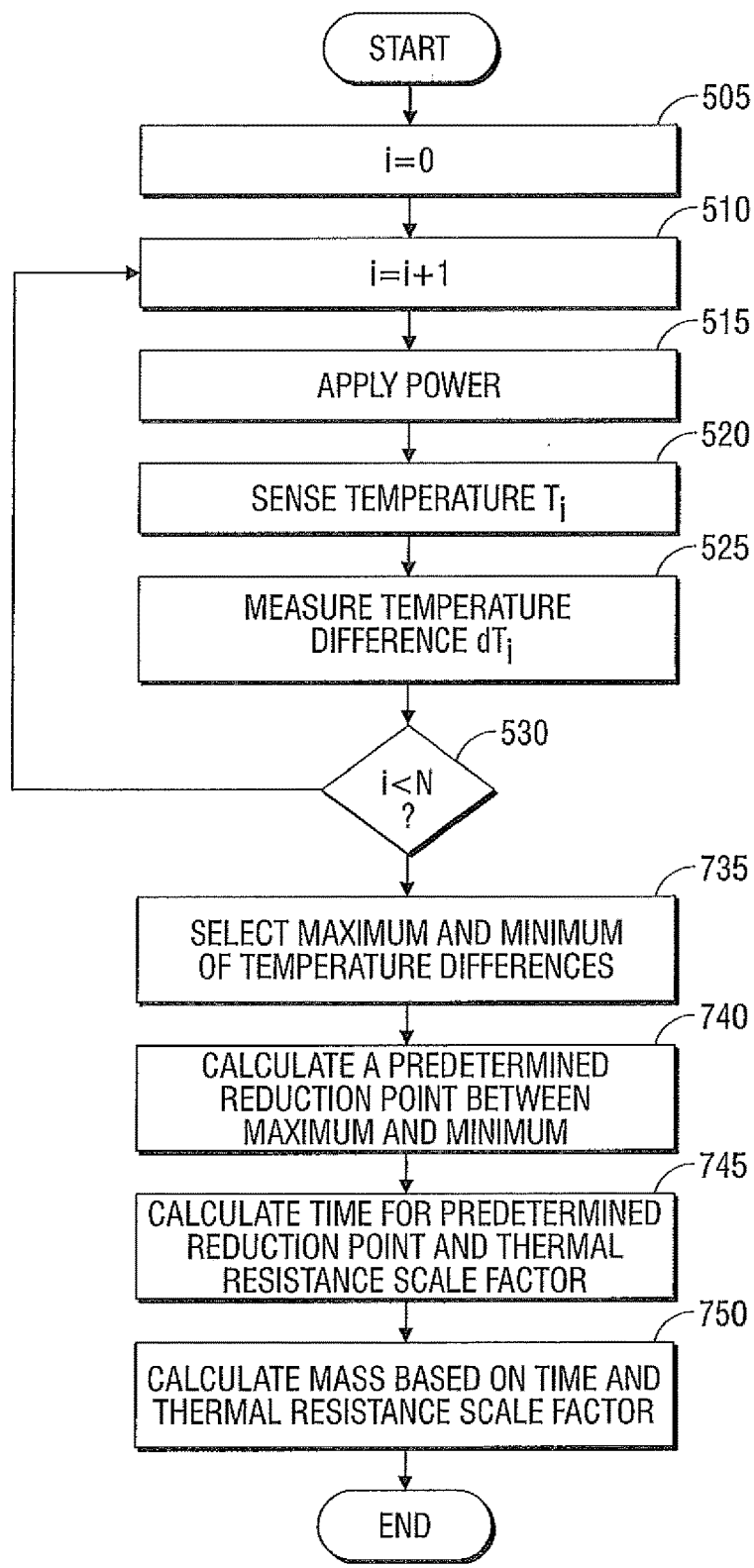
FIG. 7 is a flow diagram of a non-iterative method of estimating tissue mass and the thermal resistance scale factor in accordance with still further embodiments of the present disclosure.

The gradient descent method described in FIGS. 6A-6D is an accurate and robust method for estimating the mass and thermal resistance scale factor of tissue and/or an energy-based medical instrument. In other embodiments, simpler methods, such as the non-iterative method illustrated in FIG. 7, may be employed for estimating the mass and the thermal resistance scale factor.

In steps 505-530, tissue temperatures $T_i$ are sensed and temperature differences $dT_i$ are calculated as described above with respect to FIG. 5. The non-iterative method illustrated in FIG. 7 makes an assumption closely related to the exponentially decreasing characteristics of an exponential term in the temperature and the temperature difference equations (25) and (27). The equation for the mass of tissue $M_t$ is given by:

$$M_t = \frac{P + 2P \cdot k \cdot t - P \cdot e^{-2 \cdot k \cdot t}}{4 C_{p_t} k T_i}, \quad (36)$$

which is derived from equation (25) by solving for the mass of tissue $M_t$.

The exponential term $e^{-2 \cdot k \cdot t}$ approaches zero as time t increases and becomes negligible after a certain time period. Thus, assuming that an appropriate amount of time elapses, equation (36) can be simplified by removing the exponential term as follows:

$$M_t = \frac{P + 2P \cdot k \cdot t}{4 C_{p_t} T_t k}. \quad (37)$$

Also, the temperature difference equation (32) is a reducing function which reduces from its maximum value when t is equal to zero to its minimum value when t is equal to infinity. Equation (32) is reduced by about 63% of the maximum value when:

$$2 \cdot k \cdot t = 1. \quad (38)$$

Solving equation (38) for the thermal resistance scale factor $K_i$ results in the following equation:

$$k = \frac{1}{2 t_{63}}, \quad (39)$$

where $t_{63}$ is the time at which the maximum rate of change in tissue temperature is reduced by about 63% toward the minimum rate of change. Thus, the mass can be calculated using time $t_{63}$ and equations (37) and (39).

Referring again to FIG. 7, the thermal resistance scale factor k first involves determining the maximum and the minimum tissue temperature differences for a predetermined period during which energy is applied to the tissue in step 735. Next, in step 740, the 63% reduction point between the maximum and the minimum temperature differences is calculated according to the following equation:

$$\max(dT_i) - (\max(dT_i) - \min(dT_i)) \cdot 0.63, \quad (40)$$

where $dT_i$ is an array of tissue temperature differences for the predetermined period during which energy is applied to the tissue.

In step 745, it is determined the time $t_{63}$ at which the 63% reduction occurs. The time $t_{63}$ may be determined by using a linear interpolation algorithm where $dT_i$ is the x-axis and the time index is the y-axis. The linear interpolation algorithm is illustrated by the following equation:

$$dT_i(t_{63}) = \max(dT_i) - (\max(dT_i) - \min(dT_i)) \cdot 0.63. \quad (41)$$

The thermal resistance scale factor k is then calculated by using the time $t_{63}$ and equation (39).

In step 750, the mass may be estimated using equation (37) at a time $5^* t_{63}$ when the temperature difference $dT_i$ is theoretically decreased by about 99%. A time other than $5^* t_{63}$, e.g., $4^* t_{63}$, may be used to estimate the mass depending on the system requirements. In some embodiments of the non-iterative method, the last elements of the sensed temperature array and the corresponding time index array are used to calculate the mass estimate. The controller 260 then uses the estimated mass and the estimated thermal resistance scale factor in controlling the generator.

In another embodiment, a heat transfer coefficient h, rather than the thermal resistance scale factor, is estimated to take into consideration the heat transfer characteristics of the jaw members. The thermal resistance scale factor of equation (17) is defined by the heat transfer characteristics of the jaw members as follows:

$$k = \frac{hA}{C_{p_j} M_j} \quad (42)$$

Substituting equation (42) for the thermal resistance scale factor in equation (17) results in the following equation:

$$\frac{d}{dt} T_j = \frac{hA}{C_{p_j} M_j} (T_t(t) - T_j(t)) \quad (43)$$

where $C_{p_j}$ is the specific heat of the jaw members and $M_j$ is the mass of the jaw members.

By employing the specific heat and the mass of the jaw members, equation (16) becomes:

$$T_j = T_t(t) + \frac{C_{p_t} M_t \frac{d}{dt} T_t(t)}{hA} - \frac{\frac{d}{dt} Q_{add}(t)}{hA} \quad (44)$$

Applying equation (44) to equation (17) to eliminate the term $T_j$ results in the following equation:

$$\frac{d}{dt}\left( T_t(t) + \frac{C_{p_t} M_t \frac{d}{dt} T_t(t)}{hA} - \frac{\frac{d}{dt} Q_{add}(t)}{hA} \right) = \quad (45)$$
$$\frac{hA}{C_{p_j} M_j} \left( T_t(t) - \left( T_t(t) + \frac{C_{p_t} M_t \frac{d}{dt} T_t(t)}{hA} - \frac{\frac{d}{dt} Q_{add}(t)}{hA} \right) \right).$$

A simplified version of equation (45) can be expressed in the form of a second-order differential equation, which is given by:

$$\frac{d^2}{dt^2} T_t(t) + \frac{hA \cdot \left( \frac{C_{p_t} M_t}{C_{p_j} M_j} + 1 \right)}{C_{p_t} M_t} \frac{d}{dt} T_t(t) = \frac{hA \frac{d}{dt} Q_{add}(t)}{C_{p_j} M_j C_{p_t} M_t}. \quad (46)$$

Equation (17) may be applied to equation (43) to eliminate the term $T_t$ and the resulting equation can be expressed in the form of a second order differential equation as follows:

$$\frac{d^2}{dt^2} T_t(t) + \frac{hA \cdot \left( \frac{C_{p_j} M_j}{C_{p_t} M_t} + 1 \right)}{C_{p_j} M_j} \frac{d}{dt} T_t(t) = \frac{hA \frac{d}{dt} Q_{add}(t)}{C_{p_j} M_j C_{p_t} M_t}. \quad (47)$$

Equations (46) and (47) may be used to predict temperatures of the jaw members and the tissue, respectively. Since the rate of heat change is a form of power, i.e., $$\frac{d}{dt} Q(t) = Pwr,$$

equations (46) and (47) can also be written as:

$$\frac{d^2}{dt^2}T_t(t) + \frac{hA \cdot \left(\frac{C_{p_t}M_t}{C_{p_j}M_j}+1\right)}{C_{p_t}M_t}\frac{d}{dt}T_t(t) = \frac{hAPwr}{C_{p_j}M_jC_{p_t}M_t} \quad (48)$$

and $$\frac{d^2}{dt^2}T_t(t) + \frac{hA \cdot \left(\frac{C_{p_j}M_j}{C_{p_t}M_t}+1\right)}{C_{p_j}M_j}\frac{d}{dt}T_t(t) = \frac{hAPwr}{C_{p_j}M_jC_{p_t}M_t}, \quad (49)$$

where Pwr is the power that may be any forcing function, such as a step response, exponential, sinusoid, single pulse, two pulses, or any other suitable signal for sealing and ablation procedures. The power is controlled by the controller 260 of the generator circuitry 200. The plurality of sensors 240 sense the voltage and current at the output of the RF Amp 230 and the DMAC 272 calculates power based on the sensed voltage and current.

Second-order differential equations (48) and (49) can be used to predict the temperatures of the tissue and the jaw members based upon a known heat transfer coefficient and a known mass. Conversely, the equations (48) and (49) can be used to estimate the heat transfer coefficient and the mass based upon measured temperatures of the tissue and jaw members.

Solutions to the system of second-order differential equations given by equations (48) and (49) are very complex. However, assuming that the initial temperatures of the tissue and the jaw members are zero and simplifying the solutions to equations (48) and (49), results in the following equations for the temperature of the tissue and the jaw members:

$$T_t(t) = \frac{Pwr \cdot t}{C_{p_j}M_j + C_{p_t}M_t} + \frac{C_{p_j}^2 M_j^2 \cdot Pwr}{hA(C_{p_j}M_j + C_{p_t}M_t)^2}\left(1 - e^{-\frac{hA \cdot t}{C_{p_j}M_j}} \cdot e^{-\frac{hA \cdot t}{C_{p_t}M_t}}\right) \quad (50)$$

and $$T_j(t) = \frac{Pwr \cdot t}{C_{p_j}M_j + C_{p_t}M_t} - \frac{C_{p_j}M_j \cdot C_{p_t}M_t \cdot Pwr}{hA(C_{p_j}M_j + C_{p_t}M_t)^2}\left(1 - e^{-\frac{hA \cdot t}{C_{p_j}M_j}} \cdot e^{-\frac{hA \cdot t}{C_{p_t}M_t}}\right) \quad (51)$$

The rate of change of tissue temperature is determined by taking the derivative of equation (50) with respect to time, which results in the following equation:

$$\frac{d}{dt}T_t(t) = \frac{Pwr \cdot \left(C_{p_t}M_t + C_{p_j}M_j \cdot e^{-\frac{hA \cdot t}{C_{p_j}M_j}} \cdot e^{-\frac{hA \cdot t}{C_{p_t}M_t}}\right)}{C_{p_t}M_t(C_{p_j}M_j + C_{p_t}M_t)} \quad (52)$$

Time plays a significant role in estimating the mass of the tissue being treated and the heat transfer coefficient h. The exponential terms $$e^{-\frac{hA \cdot t}{C_{p_j}M_j}} \cdot e^{-\frac{hA \cdot t}{C_{p_t}M_t}}$$

in equations (50) and (52) are equal to one when the time is zero and become negligible as time increases. Thus, when t=0, equation (52) becomes the following equation:

$$\frac{d}{dt}T_t(t) = \frac{Pwr}{C_{p_t}M_t}. \quad (53)$$

Equation (53) implies that the mass of the tissue may be estimated with the first estimation of the change in temperature when the estimation time is close to zero. The heat transfer coefficient h may be estimated when time is large while the mass may be estimated when time is very small. When t is large enough to make the exponential terms negligibly small, equation (50) simplifies to the following equation:

$$T_t(t) = \frac{Pwr \cdot t}{C_{p_j}M_j + C_{p_t}M_t} + \frac{C_{p_j}^2 M_j^2 \cdot Pwr}{hA(C_{p_j}M_j + C_{p_t}M_t)^2}. \quad (54)$$

Equation (54) can be solved for h to obtain the following equation:

$$h = \frac{C_{p_j}^2 M_j^2 \cdot Pwr}{A\left(T_t(t)(C_{p_j}M_j + C_{p_t}M_t)^2 - Pwr \cdot t \cdot (C_{p_j}M_j + C_{p_t}M_t)\right)}. \quad (55)$$

In this way, the mass and the heat transfer coefficient of the tissue can be determined and used to estimate the temperature of the tissue.

Figure 8:
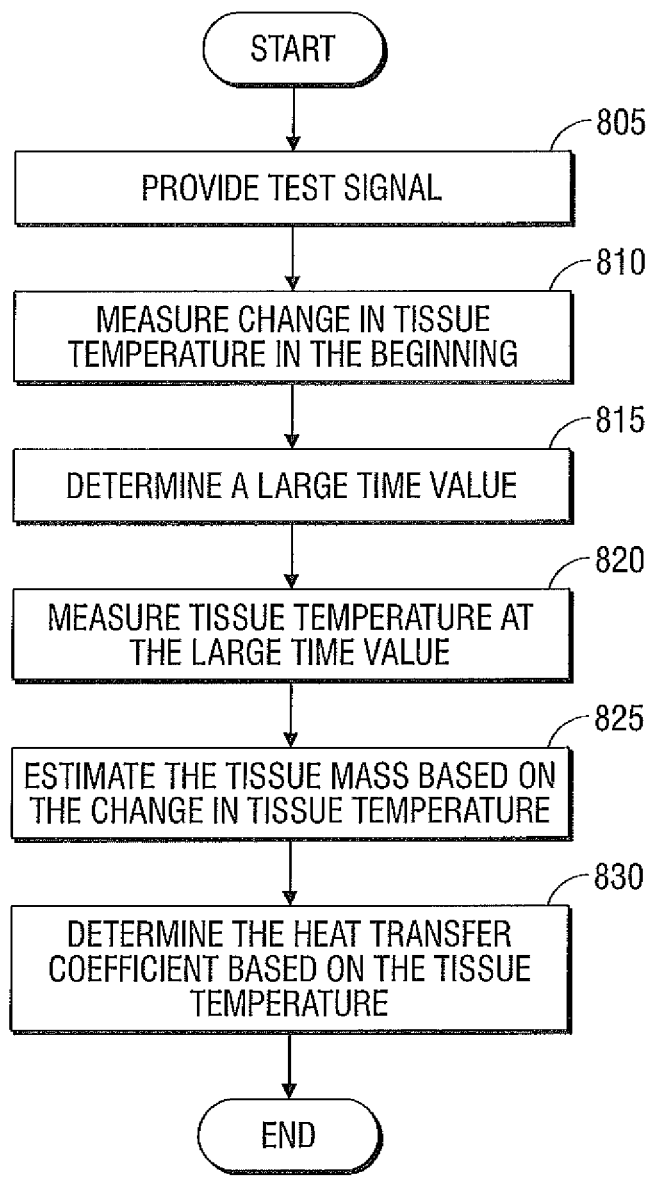
FIG. 8 is a flow diagram of a non-iterative method of estimating tissue mass and the thermal resistance scale factor in accordance with still further embodiments of the present disclosure.

A method of estimating tissue mass is illustrated in the flow diagram of FIG. 8. In step 805, a test signal is applied to the tissue to cause a measurable amount of tissue heating. In other words, the test signal is provided to cause a measurable change in tissue impedance so that a measurable change in temperature can be obtained. The test signal may include a step, an exponential signal, a sinusoid, a single pulse, multiple pulses, or any other signal suitable for causing a measurable amount of tissue heating. In step 810, a change in tissue temperature is measured as soon as possible after providing the test signal to the tissue.

In the case where temperature sensors are not used, a change in tissue impedance is estimated and then a change in the tissue temperature is estimated based on the estimated change in tissue impedance by using equation (9).

In step 815, the controller 260 determines a time value that is large enough so that the exponential term of the tissue temperature equation (51) becomes negligibly small. In step 820, tissue temperature is measured at the time value.

In step 825, by using equation (54), the tissue mass is estimated based on the power supplied by the power output stage of the generator, the rate of temperature change, and the specific heat of the tissue. A closed form solution for estimating the tissue mass is given by the equation:

$$M_t = \frac{Pwr}{C_{p_t}\frac{d}{dt}T_t(t)}. \quad (56)$$

In step 830, the heat transfer coefficient is estimated by using equation (55), which is based on tissue temperature, specific heat of the tissue and the jaw members, power, masses of the tissue and the jaw members, and the determined time. In this way, the mass and the heat transfer coefficient of the tissue may be estimated.

The time for estimating the heat transfer coefficient may be shortened by using equation (53) for estimating the heat transfer coefficient. The controller 260 measures the rate of temperature change at two times, namely, $t_1$ and $t_2$, and uses the ratio between the two rates. The ratio may be simplified and expressed as follows:

$$\text{ratio} = \frac{\frac{d}{dt}T_{t2}(t)}{\frac{d}{dt}T_{t1}(t)} = \frac{\left(C_{P_t}M_t + C_{P_j}M_j \cdot e^{-\frac{hA \cdot t_2}{C_{P_j}M_j}} \cdot e^{-\frac{hA \cdot t_2}{C_{P_t}M_t}}\right)}{\left(C_{P_t}M_t + C_{P_j}M_j \cdot e^{-\frac{hA \cdot t_1}{C_{P_j}M_j}} \cdot e^{-\frac{hA \cdot t_1}{C_{P_t}M_t}}\right)} \quad (57)$$

Equation (57) can be solved for h as follows:

$$h = -\frac{C_{P_t}M_t C_{P_j}M_j}{A(C_{P_t}M_t + C_{P_j}M_j) \cdot t_2} \ln\left(\frac{C_{P_t}M_t\left(C_{P_j}M_j \frac{d}{dt}T_{t1}(t) \cdot \text{ratio} - Pwr + C_{P_t}M_t \frac{d}{dt}T_{t1}(t) \cdot \text{ratio}\right)}{C_{P_j}M_j \cdot Pwr}\right) \quad (58)$$

The benefit of this approach is that the controller 260 does not have to wait until a time when the exponential term decreases to a negligibly small value before obtaining an estimate of the tissue mass and the heat transfer coefficient.

Figure 9:
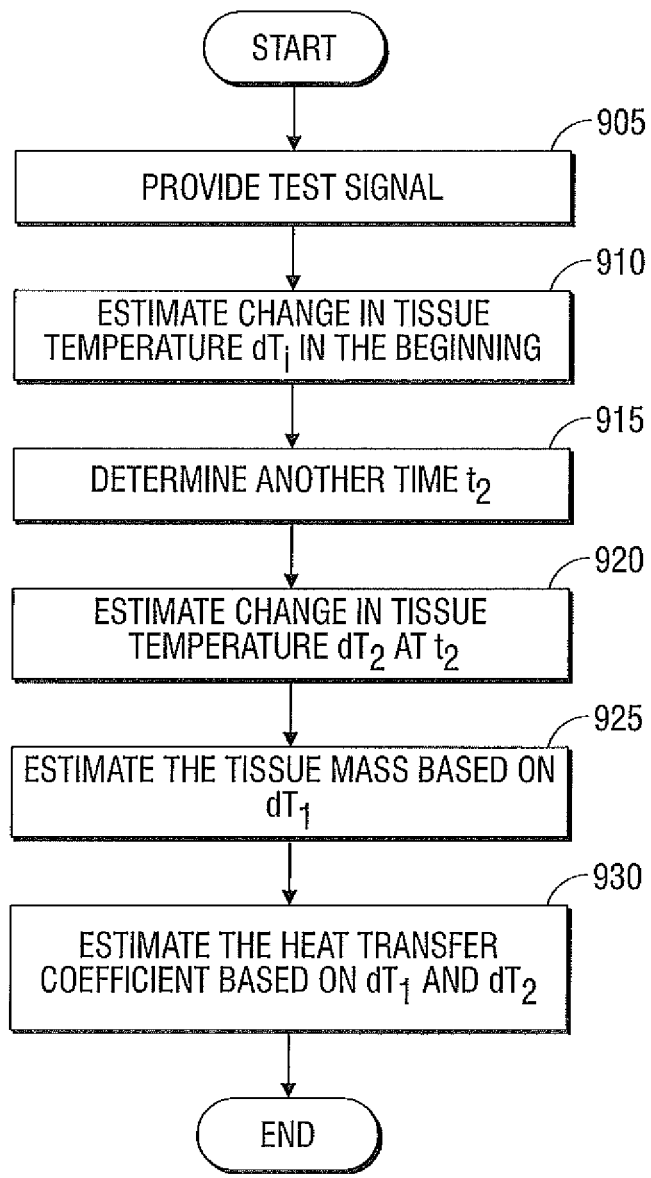
FIG. 9 is a flow diagram of a non-iterative method of estimating tissue mass and the thermal resistance scale factor in accordance with still further embodiments of the present disclosure.

FIG. 9 shows a flow diagram illustrating a method of estimating the heat transfer coefficient. In step 905, a test signal is provided to the tissue being treated. In step 910, the controller 260 estimates the temperature change $dT_1$ of the tissue at the beginning of a tissue treatment procedure. As described above, the temperature change $dT_1$ of the tissue can be measured directly by temperature sensors or can be estimated by using the equation (9) after estimating the change in tissue impedance. The earlier $dT_1$ is measured, the more accurate the estimate of the mass.

In step 915, the controller 260 determines a time $t_2$ for measuring temperature change and, in step 920, the controller 260 estimates the temperature change $dT_2$ at time $t_2$. In step 925, the tissue mass is measured by using equation (54) and, in step 930, the heat transfer coefficient h is estimated by using equation (58). In this way, the time for estimation can be shortened The methods of the present disclosure may further consider the heat transfer between the jaw members and the environment. This is represented by heat transfer equation (17), which may be expressed as:

$$\frac{dT_j}{dt} = k(T_t(t) - T_j(t)) + k_e(T_e - T_j(t)) \quad (59)$$

where $T_e$ represents the constant temperature of the environment and $k_e$ represents a thermal resistance scale factor from the jaw members to the environment. Even assuming that the initial conditions of the temperature of the tissue and the jaw members are zero and making other simplifications, the closed form solutions to the system of differential equations is very complex. However, general approximation methods can be utilized to estimate the tissue mass and the heat transfer coefficient.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. A method of determining a tissue parameter, the method comprising:
   generating a test signal using a generator;
   providing a test signal to tissue grasped by an energy delivery device;
   sensing voltage and current waveforms of the test signal;
   calculating an impedance of the grasped tissue and a change in tissue impedance based on the sensed voltage and current waveforms;
   estimating a change in tissue temperature based on the calculated impedance, the change in tissue impedance, and a heat transfer relationship between the grasped tissue and the energy delivery device; and
   estimating mass of the grasped tissue based on the estimated change in the tissue temperature.

2. The method according to claim 1, wherein the generator is a microwave generator and the energy delivery device is a microwave ablation applicator.

3. The method according to claim 1, wherein the generator is an electrosurgical generator and the energy delivery device is an electrosurgical instrument.

4. The method according to claim 1, further comprising:
   determining a time at which a rate of change in tissue temperature remains substantially constant;
   measuring the tissue temperature at the determined time; and
   estimating a heat transfer coefficient between the grasped tissue and the energy delivery device based on the measured tissue temperature and the estimated mass of the grasped tissue.

5. The method according to claim 4, wherein the parameters include a surface area of an electrode of an electrosurgical instrument that contacts the grasped tissue, the mass of the electrode, and the heat transfer coefficient of the electrode.

6. The method according to claim 4, wherein the estimated heat transfer coefficient is based on a system of second-order differential equations of tissue temperature changes.

7. The method according to claim 1, wherein the change in tissue temperature is estimated based on the calculated impedance by using an equation relating tissue temperature changes to tissue impedance changes.

8. The method according to claim 7, wherein the change in tissue temperature is estimated based on the calculated impedance and parameters of the energy delivery device.

9. The method according to claim 1, wherein the energy delivery device is a vessel sealing device.

10. A method of determining a tissue parameter, the method comprising:
    generating a test signal using a generator;
    providing the test signal to tissue grasped by an energy delivery device;
    sensing voltage and current waveforms of the test signal;
    estimating a first impedance of the grasped tissue based on the sensed voltage and current waveforms;
    estimating a first change in temperature of the grasped tissue based on a heat transfer relationship between the grasped tissue and the energy delivery device at a first time based on the first impedance;
    estimating a second impedance of the grasped tissue;

estimating a second change in temperature of the grasped tissue based on a heat transfer relationship at a second time based on the second impedance;

estimating mass of the grasped tissue based on the first change in tissue temperature;

estimating a heat transfer coefficient between the grasped tissue and the energy delivery device based on the first and second changes in tissue temperature.

11. The method according to claim 10, wherein the generator is a microwave generator and the energy delivery device is a microwave ablation applicator.

12. The method according to claim 10, wherein the generator is an electrosurgical generator and the energy delivery device is an electrosurgical instrument.

13. The method according to claim 10, wherein the first and second changes in tissue temperature are estimated based on the first and second estimated tissue impedances, respectively, by using an equation relating tissue temperature changes to tissue impedance changes.

14. The method according to claim 13, wherein the first and second changes in tissue temperature are estimated based on the first and second estimated tissue impedances, respectively, and parameters of the energy delivery device.

15. The method according to claim 14, wherein the parameters of the energy delivery device include a surface area of that portion of the energy delivery device that contacts the grasped tissue, a mass of at least a portion of the energy delivery device, and a heat transfer coefficient of the at least a portion of the energy delivery device.

16. The method according to claim 10, wherein the mass and the heat transfer coefficient are estimated based on a system of second-order differential equations of tissue temperature changes.

17. The method according to claim 10, wherein the energy delivery device is a vessel sealing device.

* * * * *